(12) United States Patent
Zaleski et al.

(10) Patent No.: US 6,828,439 B1
(45) Date of Patent: Dec. 7, 2004

(54) COMPOUNDS, COMPOSITION, AND METHODS FOR PHOTODYNAMIC THERAPY

(75) Inventors: Jeffrey M. Zaleski, Bloomington, IN (US); Diwan Singh Rawat, Bloomington, IN (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/913,924

(22) PCT Filed: Feb. 25, 2000

(86) PCT No.: PCT/US00/04915
§ 371 (c)(1),
(2), (4) Date: Aug. 20, 2001

(87) PCT Pub. No.: WO00/50117
PCT Pub. Date: Aug. 31, 2000

Related U.S. Application Data

(60) Provisional application No. 60/122,097, filed on Feb. 26, 1999.

(51) Int. Cl.$^7$ ................................................ C07F 11/00
(52) U.S. Cl. ............................ 546/2; 534/15; 540/465; 540/488; 546/10; 564/374; 568/729; 568/807
(58) Field of Search .................. 546/2, 10, 9; 540/465, 540/486, 121, 145; 534/15; 564/374; 568/729, 807

(56) References Cited

U.S. PATENT DOCUMENTS

| | | | |
|---|---|---|---|
| 5,371,199 A | 12/1994 | Therien et al. | 534/11 |
| 5,986,090 A | 11/1999 | Therien et al. | 540/145 |
| 6,043,237 A | 3/2000 | Meadows et al. | 514/185 |
| 6,514,995 B1 | 2/2003 | Zaleski et al. | 514/332 |

OTHER PUBLICATIONS

Nicolaou et al. "Molecular Design and Chemical Synthesis of Potent Enediynes" *Chem. Abst.*, vol. 117: 233658v and 233659w, p. 835 (1992).
Ali et al., "Metal Complexes as Photo– and Radiosensitizers," *Chem. Rev.*, 99, 2379–2450 (1999).
Basak et al., "The Synthesis and Reactivity of Novel Azetidinyl Enediynes," *Chem. Commun.*, 749–750 (1996).
Bergman, "Reactive 1,4–Dehydroaromatics," *Accounts of Chemical Research*, 6, 25–31 (1973).
Bonadies et al., "Vanadium Phenolates as Models for Vanadium in Biological Systems. 1. Synthesis, Spectroscopy, and Electrochemistry of Vanadium Complexes of Ethylenebis [(o–hydroxyphenyl)glycine] and its Derivatives," *J. Am. Chem. Soc.*, 108, 4088–4095 (1986).
Bonnett, "Photosensitizers of the Porphyrin and Phtalocyanine Series for Photodynamic Therapy," *Chem. Soc. Reviews*, 24, 19–33 (1995).

Boyle et al., "Structure and Biodistribution Relationships of Photodynamic Sensitizers," *Photochemistry and Photobiology*, 64 (3), 469–485 (1996).
Branca et al., "Formation and Structure of the Tris(catecholato)vanadate(IV) Complex in Aqueous Solution," *Inorg. Chem.*, 29, 1586–1589 (1990).
Chapman et al., "9,10–Dehydroanthracene. A Derivative of 1,4–Dehydrobenzene," *J. Am. Chem. Soc.*, 98 (18), 5703–5705 (1976).
Christner et al., "Unmasking the Chemistry of DNA Cleavage by the Esperamicins: Modulation of 4'-Hydrogen Abstraction and Bistranded Damage by the Fucose–Anthranilate Moiety," *J. Am. Chem. Soc.*, 114, 8763–8767 (1992).
Churcher et al., "Synthesis of the Enediyne Aglycone (±)–Calicheamicinone," *J. Am. Chem. Soc.*, 120, 3518–3519 (1998).
Cummings et al., "Luminescent Platinum (II) Complexes of Quinoxaline–2,3–dithiolate," *Inorg. Chem.*, 34, 2007–2014 (1995).
Cummings et al., "Tuning the Excited–State Properties of Platinum (II) Diimine Dithiolate Complexes," *J. Am. Chem. Soc.*, 118, 1949–1960 (1996).
Dai et al., "Synthesis and DNA Clavage Study of a 10–Membered Ring Enediyne Formed via Allylic Rearrangement," *J. Org. Chem.*, 64, 682–683 (1999).
Evenzahav et al., "Photochemical Rearragement of Endiynes: Is a "Photo–Bergman" Cyclization a Possibility?" *J. Am. Chem. Soc.*, 120, 1835–1841 (1998).
Funk et al., "Photochemical Cycloaromatization Reactions of ortho–Dialkynylarenes: A New Class of DNA Photocleaving Agents," *J. Am. Chem. Soc.*, 118, 3291–3292 (1996).
Golik et al., "Esperamicins, a Novel Class of Potent Antitumor Antibiotics. 2. Structure of Esperamicin X," *J. Am. Chem. Soc.*, 109, 3461–3462 (1987).
Golik et al., "Esperamicns, a Novel Class of Potent Antitumor Antibiotics. 3. Structures of Esperamicins A1, A2, and A1b," *J. Am. Chem. Soc.*, 109, 3462–3464 (1987).
Hangeland et al., "Specific Abstraction of the 5'(S)– and 4'–Deoxyribosyl Hydrogen Atoms from DNA by Calicheamicin $\gamma_1$," *J. Am. Chem Soc.*, 114, 9200–9202 (1992).

(List continued on next page.)

*Primary Examiner*—Richard L. Raymond
(74) *Attorney, Agent, or Firm*—Leydig, Voit, Mayer, Ltd.

(57) ABSTRACT

Disclosed are novel compounds, compositions, and methods that are particularly useful in photodynamic therapy. In particular, the inventive compounds, compositions, and methods relate to the formation of cytotoxic radical species in the presence of light. Significantly, the compounds, compositions, and methods of the present invention do not require the presence of oxygen in the photodynamic therapy and, as such, rely on a unimolecular mechanism for producing the radicals. The inventive compounds, compositions, and methods can be used, for example, in the treatment of cancers as well as infections caused by microorganisms such as protozoa, fungi, bacteria, and viruses.

20 Claims, 10 Drawing Sheets

OTHER PUBLICATIONS

Holmes et al., "Models for the Binding Site in Bromoperoxidase: Mononuclear Vanadium (V) Phenolate Complexes of the Hydridotris(3,5–dimethylpyrazolyl)borate Ligand," *Inorg. Chem., 30*, 1231–1235 (1991).

Kaneko et al., "Photochemical Cycloaromatization of Non–Benzenoid Enediynes," Angew. Chem. Int. Ed., 38 (9), 1267–1268 (1999).

Kim et al., "Rapid Bergman Cyclization of 1,2–Diethynyl-heteroarenes," *J. Org. Chem., 63*, 8229–8234 (1998).

Konig et al., "Activation of Macrocyclic Biaryl–Enediynes by Metal Ion Coordination," *Angew. Chem. Int. Ed. Engl., 34*(22), 2538–2540 (1995).

Konig et al., "Synthesis, Structure, and Reactivity of Enediyne Macrocycles," *J. Org. Chem., 61*, 4258–4261 (1996).

Kusakabe et al., "Conformation–Selective DNA Strand Breaks by Dynemicin: A Molecular Wedge into Flexible Regions of DNA," *Biochemistry, 32*, 11669–11675 (1993).

Lee et al., "Calicheamicins, a Novel Family of Antitumor Antibiotics. 4. Structure Elucidation of Calicheamicins $\beta_1^{Br}$, $\gamma_1^{Br}$, $\alpha_2^{I}$, $\alpha_3^{I}$, $\beta_1^{I}$, $\gamma_1^{I}$, and $\delta_1^{I}$," *J. Am. Chem. Soc., 114*, 985–997 (1992).

Leet et al., "Chemistry and Structure Elucidation of the Kedarcidin Chromophore," *J. Am. Chem. Soc., 115*, 8432–8443 (1993).

Li et al., "Vanadium Complexes of the Tridentate Schiff Base Ligand N–Salicylidene–N'–(2–Hydroxyethyl)ethylenediamine: Acid–Base and Redox Conversion between Vanadium (IV) and Vanadium (V) Imino Phenolates," *Inogr. Chem., 27*, 4657–4664 (1988).

Lockhart et al., "Evidence for the Reactive Spin State of 1,4–Dehydrobenzenes," *J. Am. Chem. Soc., 103*, 4091–4096 (1981).

Magnus et al., "Synthetic and Mechanistic Studies on Esperamicin $A_1$ and Calicheamicin $\gamma_1$. Molecular Strain Rather Than n–Bond Proximity Determines the Cycloaromatization Rates of Bicyclo[7.3.1] Enediynes," *J. Am. Chem. Soc., 112*, 4986–4987 (1990).

Maier, "Design of Enediyne Prodrugs," *Synlett*, 13–26 (1995).

Marthur et al., "Cytosine Methylation Enhances DNA Damage Produced by Groove Binding and Intercalating Enediynes: Studies with Esperamicins A1 and C," *Biochemistry, 36*, 14868–14873 (1997).

Minami et al., "Structure of an Aromatization Product of C–1027 Chromophore," *Tetrahedron Letters, 34* (16), 2633–2636 (1993).

Myers et al., "Design and Synthesis of a System of Enediyne Formation by Anthraquinone Reductive Activation," *J. Am. Chem. Soc., 114*, 5859–5860 (1992).

Myers et al., "Total Synthesis of (+)–Neocazinostatin Chromophore," *J. Am. Chem. Soc., 120*, 5319–5320 (1998).

Kappen et al., "Replication Block by an Enediyne Drug–DNA Deoxyribose Adduct," Biochemistry, 38, 235–242 (1999).

Nicolaou et al., "Cyclic conjugated Enediynes Related to Calicheamicins and Esperamicins: Calculations, Synthesis, and Properties," *J. Am. Chem. Soc., 110*, 4866–4868 (1988).

Nicolaou et al., "Synthesis and Chemistry of Dynemicin A Models," *J. Am. Chem. Soc., 113*, 3106–3114 (1991).

Nicolaou et al., "Enediyne Compounds equipped with Acid–, Base– and Photo–Sensitive Triggering Devices. Chemical Simulation of the Dynemicin A Reaction Cascade," *Angew. Chem. Int. Ed. Engl., 30* (8), 1032–1036 (1991).

Nicolaou et al., "Design, Synthesis, and Study of Simple Monocyclic Conjugated Enediynes. The 10–Membered Ring Enediyne Moiety of the Enediyne Anticancer Antibiotics," *J. Am. Chem. Soc., 114*, 7360–7371 (1992).

Nicolau et al., "Redox–Controlled Bergman Cycloaromatizations. Designed Enediynes with DNA–Cleaving Properties and Antitumor Activity," *J. Am. Chem. Soc., 114*, 9279–9282 (1992).

Nicolaou et al., "Chemistry and Biology of Natural and Designed Enediynes," *Proc. Natl. Acad. Sci. USA , 90*, 5881–5888 (1993).

O'Brien et al., "Action Spectra of the Antileukemic and Antiviral Activities of Merocyanine 540," *Photochemistry and Photobiology, 54* (5), 851–854 (1991).

Oseroff et al., "Strategies for Selective Cancer Photochemotherapy; Antibody–Targeted and Selective Carcinoma Cell Photolysis," *Photochemistry and Photobiology, 46* (1), 83–96 (1987).

Pandey et al., "Porphyrin Dimers as Photosensitizers in Photodynamic Therapy," *J. Med. Chem., 33*, 2032–2038 (1990).

Pandey et al., "Synthesis, Photophysical Properties, in Vivo Photosensitizing Efficacy, and Human Serum Albumin Binding Properties of Some Novel Bacteriochlorins," *J. Med. Chem., 40*, 2770–2779 (1997).

Ramkumar et al., "Cyclization of Enediyne Radical Cations through Chemical, Photochemical and Electrochemical Oxidation: The Role of State Symmetry," *J. Org. Chem., 61*, 2247–2250 (1996).

Ressler et al., "Creating New Photosensitizers for Cancer Therapy," *Chemtech, 28* (3), 39–45 (1998).

Schreiner, "Cyclic Enediynes: Relationship between Ring Size, Alkyne Carbon Distance, and Cyclization Barrier," *Chem. Commun.*, 483–484 (1998).

Schreiner, "Monocyclic Enediynes: Relationships between Ring Sizes, Alkyne Carbon Distances, Cyclization Barriers, and Hydrogen Abstraction Reactions. Sunglet–Triplet Separations of Methyl–Substituted p–Benzynes," *J. Am. Chem. Soc., 120*, 4184–4190 (1998).

Sessler et al., "Texaphyrins: Synthesis and Applications," *Acc. Chem. Res., 27*, 43–50 (1994).

Shain et al., "The Synthesis and Reactivity of a Novel 10–Membered Azaenediyne," *Tetrahedron Letters, 38* (34), 6067–6070 (1997).

Shair et al., "The Total Synthesis of Dynemicin A Leading to Development of a Fully Contained Bioreductively Activated Endiyne Prodrug," *J. Am. Chem. Soc., 118*, 9509–9525 (1996).

Shiraki et al., "Visible Light Induced DNA Cleavage by the Hybrid Antitumor Antibiotic Dynemicin A," *Biochemistry*, 29 9795–9798 (1990).

Smith et al., "The Enediyne Antibiotics," *Journal of Medicinal Chemistry, 39* (11), 2103–2117 (1996).

Sugiura et al., "DNA Intercalation and Cleavage of an Antitumor Antibiotic Dynemicin that Contains Anthracycline and Enediyne Cores," *Proc. Natl. Acad. Sci. USA, 87*, 3831–3835 (1990).

Turro et al., "Photochemical Analogue of the Bergman Cycloaromatization Reaction," *Tetrahedron Letters, 35* (44), 8089–8092 (1994).

Warner et al., "Controlled Acceleration and Inhibition of Bergman Cyclization by Metal Chlorides," *Science, 269*, 814–816 (1995).

Wells, "Cancer Gets the Red Light. Pharmacyclics, Inc.," *Chemistry & Biology, 4* (10), 775–776 (1997).

Wender et al., "A Photochemically Triggered DNA Cleaving Agent; Synthesis, Mechanistic and DNA Cleavage Studies on a New Analog of the Antitumor Antibiotic Dynemicin," *J. Org. Chem., 58* (22), 5867–5869 (1993).

Wisniewski Grissom et al., "Determination of the Activation Parameters for the Bergman Cyclization of Aromatic Enediynes," *J. Org. Chem., 59*, 5833–5835 (1994).

Xi et al., "Mechanistic Studies on the Base–Catalyzed Transformation of Neocarzinostatin Chromophore: Roles of Bulged DNA," *Biochemistry, 38*, 4342–4354 (1999).

Xu et al., "Mechanism of Formation of Novel Covalent Drug DNA Interstrand CrOss–Links and Monoadducts by Enediyne Antitumor Antibiotics," *Biochemistry, 36*, 14975–14984 (1997).

Xu et al., "DNA Damage Produced by Enediynes in the Human Phosphoglycerate Kinase Gene In Vivo: Esperacmicin A1 as a Nucleosome Footprinting Agent," *Biochemistry, 37*, 1890–1897 (1998).

Zein et al., "Calicheamicin $\gamma_1^I$ : An Antitumor Antibiotic That Cleaves Double–Stranded DNA Site Specifically," Science, 240, 1198–1201 (1988).

Zein et al., "Exclusive Abstraction of Nonexchangeable Hydrogens from DNA by Calicheamicin γ1," *J. Am. Chem. Soc., 111*, 6888–6890 (1989).

Zein et al., "Calicheamicin $\gamma_1^I$ and DNA: Molecular Recognition Process Responsible for Site–Specificity," *Science, 244*, 697–699 (1989).

(4)

(5)

US 6,828,439 B1

COMPOUNDS, COMPOSITION, AND METHODS FOR PHOTODYNAMIC THERAPY

This application is a 371 of PCT/US00/04915, filed Feb. 25, 2000, which claims benefit of U.S. Provisional Application No. 60/122,097, filed Feb. 26, 1999.

TECHNICAL FIELD OF THE INVENTION

The present invention pertains generally to photodynamic therapy, as might be particularly useful in the treatment of cancers, viruses, and bacteria.

BACKGROUND OF THE INVENTION

Photodynamic therapy (PDT) has been used widely in the treatment of a variety of cancers, including breast metastases, gynecological tumors, cutaneous cancers, Karposi's sarcoma, and papillomatosis. In general, PDT has involved localization of a chromophoric dye molecule (e.g., porphyrins, chlorins, pheophorbides, and phthalocyanines) at a cancerous site, followed by optical excitation of the dye at relatively long wavelengths (e.g., $\lambda$=650 nm or higher), where the transparency of human tissue is significant.

Particularly, the chromophore-containing dye molecule in its natural or ground state is a singlet (i.e., $^1\pi\pi$) such that the two electrons in the highest occupied molecular orbital are paired. Upon optical excitation, the photoexcited $^1\pi\pi^*$ state of the dye molecule decays non-radiatively to a triplet (i.e., $^3\pi\pi^*$) state, which is lower in energy than the photoexcited singlet state of the dye molecule. In its triplet state, the dye molecule is then reacted with oxygen, which in its ground state is a triplet (i.e., $^3O_2$). By way of a triplet-triplet annihilation mechanism, the excited triplet state of the dye molecule and the ground state (triplet) oxygen react to produce the ground state dye molecule and oxygen in the singlet state (i.e., $^1O_2$), which is non-selectively cytotoxic. In this manner, existing PDT methods attempt to control the chemical decomposition of carcinogenic cells through selective optical initiation at wavelengths exhibiting moderate tissue penetration.

Photofrin®, which is commercially available from QLT Phototherapeutics of Vancouver, British Columbia, is an example of a porphyrin type of compound (i.e., hematoporphyrin dimer) that utilizes this bimolecular triplet state mechanism to achieve photodynamic therapy. Indeed, Photofrin® has been used to treat esophageal, lung, bladder, gastric, and cervical cancers. In addition, some PDT studies have also been successful in treating viruses, such as papillomavirus, HIV, herpes simplex virus, measles and simian virus.

However, existing PDT approaches have been fraught with a number of disadvantages, primarily relating to the underlying bimolecular nature of these PDT approaches. In particular, existing PDT approaches have not been satisfactory for practical use in hypoxic environments because of the inherent reliance on the accessibility of oxygen. In addition, the fact that the cytotoxic process is based on freely diffusing singlet oxygen, $^1O_2$, which is very reactive, is problematic because of the danger of generating unwanted reactions. Also, the effectiveness of PDT agents diminishes as photolysis times increase due to capillary collapse and a resulting restriction in blood flow, thereby causing reduced availability of $O_2$. In this respect, the primary mechanism of existing bimolecular, oxygen-reliant PDT methods is vascular stasis, which halts the flow of oxygen and nutrients to tumor cells. As such, the lack of available oxygen inhibits the further effectiveness of the PDT agent to perform its function.

Apart from PDT, another class of anticancer agents pertain to calicheamicin and esperamicin enediynes. One feature of these systems is the unusual (Z)-1,5-diyne-3-ene unit that undergoes Bergman cyclization to produce a 1,4-benzenoid diradical. This species provides the thermodynamic driving force for the DNA-cleaving reaction by promoting H-atom abstraction from the deoxyribose ring. Formation of the diradical intermediate can be triggered by the presence of reducing agents such as NADPH or dithiothrietol.

Within this class, dynemicin-A is unique in that in addition to the reactive enediyne moiety, it also contains an anthraquinone chromophore that is responsible for the deep violet color of the molecule. The proposed mechanism of action of dynemicin-A suggests that reduction of the anthraquinone subunit induces epoxide ring opening, followed by tautomerization and Bergman cyclization of the enediyne linkage to produce a reactive benzene diradical intermediate that affords DNA-strand scission through H-atom abstraction. Unfortunately, these known enediynes have been ill-suited for use in in vivo treatments because of the high thermal reactivity and prominent synthetic challenges involved in obtaining the enediynes in sufficient quantities.

In addition to diradical-forming enediyne antibiotics, recent reports have shown that the terminal diazo-containing class of natural products including kinamycin C and prekinamycin are functional DNA-cleaving agents that utilize $N_2$-release for activity. After their discovery, simple 9-diazofluorenes and other synthetic analogs have been prepared and shown very recently to induce thermal DNA-cleavage as well as photochemical strand scission upon UV excitation. Several different intermediates have been proposed to be involved in the DNA-cleavage process including both oxidative and reductive radicals as well as carbenes and a protonated form of 9-diazofluorene. However, existing terminal diazo compounds have not been fully satisfactory for use in in vivo treatments because they are simple organic compounds that do not have sufficiently long wavelength absorption features.

From the foregoing, it will be appreciated that there exists a need in the art for an approach for photodynamic therapy in which a chromophore is coupled to a photochemically reactive subunit that does not require oxygen as a coreagent. In this respect, there is a need for a photodynamic therapy approach that utilizes a unimolecular system that overcomes the drawbacks of oxygen-dependent photochemistry and functions in hypoxic environments without compromising the selectivity of optical initiation. There is also a need for a PDT approach in which sufficient quantities of desired compounds can be synthetically obtained readily and which is not subject to high thermal reactivity. It is an object of the present invention to provide such a photodynamic therapy approach that satisfies these needs. These and other objects and advantages of the present invention, as well as additional inventive features, will be apparent from the description of the invention provided herein.

BRIEF SUMMARY OF THE INVENTION

The present invention provides novel compounds, compositions, and methods for photodynamic therapy which function by a unimolecular mechanism. Significantly, pursuant to the unimolecular mechanism, the inventive compounds, compositions, and methods do not require the presence of oxygen as a co-reagent to function in photodynamic therapy. Since it has been found that the compounds, compositions, and methods of the present invention perturb DNA (as described below), it is expected that the compounds, compositions, and methods of the present invention have significant utility in treating cancers as well as infections caused by microorganisms.

In accordance with the present invention, the compounds, compositions, and methods involve the formation of radical species for treating the cancers and/or infections. Desirably, the radicals are photochemically-induced (e.g., at visible wavelengths above 400 nm). In this respect, a therapeutically effective amount of a compound capable of forming a radical upon exposure to light by a unimolecular mechanism (e.g., in the absence of oxygen) is administered (e.g., by injection) to a patient so as to contact the cancer or microorganism selected for treatment. The compound is then irradiated at the site of action so as to induce radical formation. Strictly by way of example, the compounds can include metalloenediynes (i.e., transition metal complexes with metal chelating enediyne ligands) and/or transition metal complexes that bear at least one diazo functional group, such as, but not limited to, a terminal diazo group or as in a triazine (also generally referred to herein as "transition metal diazo compounds" or "transition metal diazo complexes").

Advantageously, the compounds, compositions, and methods of the present invention can be used in photodynamic therapy such that the presence of oxygen is not required in conjunction with light. As such, the compounds, compositions, and methods of the present invention can even function in hypoxic environments without compromising the selectivity of optical initiation. Also, desired compounds pursuant to the present invention exhibit high air and thermal stability, as well as high water solubility, which are particularly desirable attributes for photonucleases for photodynamic therapy applications. In addition, the inventive compounds, compositions, and methods also permit triggering of the photochemical reactivity in a controlled manner for biological applications. Furthermore, desired compounds can be synthetically obtained readily.

The present invention will be more fully understood upon reading the following detailed description in conjunction with the accompanying drawings.

DETAILED DESCRIPTION

Figure 1:
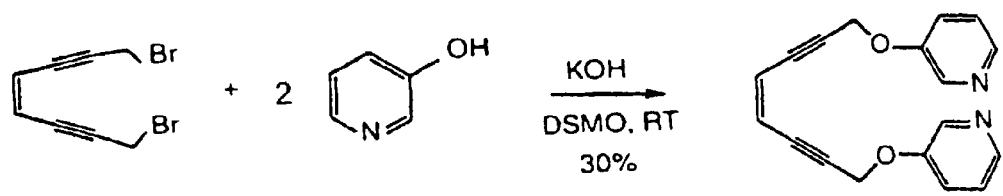
FIG. 1 schematically illustrates the synthesis of 1,2,-bis(pyridine-3-oxy)oct-4-ene-2,6-diyne, i.e., compound "1", by nucleophilic $S_N2$ substitution.

The present invention is predicated, at least in part, on providing compounds, compositions, and methods for photodynamic therapy in which radicals (including diradicals and/or monoradical cations or anions) are formed in the presence of light. For purposes of the present invention, the term "radical" refers to at least one unpaired electron, and in the case of two unpaired electrons, they can be on the same carbon center or different carbon centers. Accordingly, the terms "radicals" and "diradicals" encompass carbenes in the context of the present invention. The compounds form intermediates (that bear the radicals) in the presence of light by a unimolecular mechanism. By virtue of the unimolecular mechanism, the presence of oxygen is not required in the photodynamic therapy applications of the inventive compounds, compositions, and methods.

Significantly, the radicals perform hydrogen atom abstraction (also referred to as "H atom abstraction") In this respect, the radical-containing intermediates "take" (i.e., react with to remove) hydrogen atoms from a DNA backbone (e.g., from cancerous cells or a microorganism within a host) to which it is exposed to satisfy the intermediate radical thereby forming a DNA radical and resulting in DNA cleavage, wherein it is believed that the DNA ribose ring opens.

In particular, the compounds, compositions, and methods of the present invention can be utilized in photodynamic therapy applications involving, for example, the treatment of cancers and/or infections caused by microorganisms. For example, the types of cancer that can be treated using the inventive compounds, compositions, and methods, include, but are not limited to, breast metastases, gynecological tumors, cutaneous cancers, Karposi's sarcoma, papillomatosis, and the like. The compounds, compositions, and methods of the present invention can also be utilized to combat microorganisms, such as, for example, fungi, bacteria, viruses, protozoa, and the like.

The inventive compounds can also be used to study the life cycle of, for example, cancers, viruses, and microorganisms. By way of example, by examining the molecules with which compounds according to the invention interact, and by examining the stage in the life cycle in which the cancer, virus, organism, or the like is susceptible to the compounds, the skilled artisan can infer that the interacting molecule (to which the inventive compounds bind) is critical or important in regulating life cycle, cell permeability, or the like. The inventive compounds may also be useful for determining the mechanism of action of other compounds that work on the same cancer, virus, organism, or the like, for example, if one obtains the same result with or without addition of other pharmacoactive compounds, then a strong suggestion is that the two compounds regulate the same event. Moreover, with respect to microorganisms and viruses, the inventive compound can be used as a topical antiseptic on laboratory and other surfaces. Meanwhile, with respect to cancer, the inventive compounds can be used in separating non-transformed cells from a population of transformed cells.

Desirably, the compounds, compositions, and methods of the present invention can be used locally to treat cancers and/or infections caused by microorganisms. For example, after determining a locus in a patient (e.g., a mammal) in which a microorganism or cancer is situated, a compound which is capable of forming a radical-containing intermediate by a unimolecular mechanism upon exposure to light is locally delivered to the locus (e.g., by injection). If desired, the compound can be combined with a suitable pharmaceutically acceptable carrier (as will be appreciated readily by one of ordinary skill in the art), especially injectable carriers, to form a pharmaceutical composition. Visible radiation can then be initiated at the locus in the presence of the compound (as will be appreciated by one of ordinary skill in the art, for example, by a fiber optic probe connected to an external illuminating source or otherwise surgically exposing the locus to light at the desired wavelength) to generate the radical photochemically. In this respect, the wavelength of the light is preferably at least about 400 nm, more preferably at least about 600 nm, and even more preferably at least about 700 nm, such that tissue penetration is enhanced. Accordingly, compounds that generate radicals at wavelengths of at least 400 nm (preferably at least about 600 nm, more preferably at least 700 nm) and have suitable absorptivity (e.g., exhibiting extinction coefficients of at least about 10 $M^{-1}cm^{-1}$, preferably at least about 100 $M^{-1}cm^{-1}$, more preferably at least about 1000 $M^{-1}cm^{-1}$) are preferred.

For example, compounds that are particularly useful in the context of the present invention for forming a radical-containing intermediate by a unimolecular mechanism include, but are not limited to, metalloenediyne complexes (comprising transition metals) as well as transition metal diazo complexes. Both the metalloenediynes and the transition metal diazos form radicals in the presence of light without requiring a co-reagent (such as oxygen). In this regard, the metalloenediynes form a radical-containing intermediate by rearranging the enediyne bridge (e.g., taking an electron from each of the triple bonds to form a six-membered ring bearing one extra electron on two different carbons, as in a Bergman cyclization), while the transition metal diazos form the radical-containing intermediate by di-nitrogen loss of a diazo (i.e., —N=N—) unit.

In accordance with the present invention, while any suitable transition metal can be utilized, the transition metals utilized in the metalloenediyne and transition metal diazo complexes preferably are redox active transition metals, such as, for example, Cu(I), Cu(II), Ru, V, Ti, Zr, lanthanides, Fe(III), Pt(II), Pd(O), and Pd(II). In this respect, while the enediyne and diazo functional groups, respectively, include the sites of radical formation, the other portions of the respective metalloenediyne and transition metal diazo molecules are selected to optimize the photactivation properties of the compounds useful in the context of the present invention. By way of example, the transition metal of both the metalloenediyne and diazo complexes are selected to enhance the photoselectivity and thermal properties (e.g., desirably, the radicals form in the presence of light at physiological temperatures) of the compounds.

While not wishing to be bound by any particular theory, it is believed that the thermal chemistry and photactivation properties of the novel metalloenediyne and transition metal diazo complexes are based on metal complex geometry and/or metal ligand charge-transfer states. Mechanistically, with respect to molecular orbitals, it is believed that, upon exposure to light, the transition metal is reducing (i.e., putting electron density in the π orbital) or oxidizing the enediyne linkage (i.e., removing an electron from the triple bond). In any event, it is believed that the transition metal reduces the bond order and converts the triple bond to a double bond thereby converting the compound to a diradical-containing transition state made of three double bonds from which the cyclization can be completed (e.g., by way of H-atom abstraction as perhaps from a DNA backbone). Since it is believed that the metal provides an electron for the enediyne π orbital or removes an electron from the triple bond, it is believed that redox active transition metals (as noted above) are particularly desirable.

Similarly, with respect to the transition metal diazo complexes, it is also believed that the transition metal governs the energy of the optical absorption band of the diazo functional group. In particular, the transition metal is selected to activate the di-nitrogen release that results in the formation of the radical-containing intermediate, which has the ability to perform H-atom abstraction with, for example, DNA. As is the case with metalloenediynes, it is believed that redox active transition metals are particularly desirable for activating di-nitrogen release.

With respect to metalloenediynes, in accordance with an aspect of the present invention, a novel compound is provided having the following formula:

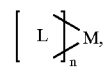

In particular, M is a metal selected from Ti, V, Mn, Fe, Co, Ni, Cu, Zn, Ga, Tb, Eu, Gd, Dy, Lu, Zr, Nb, Mo, Te, Ru, Rh, Pd, Ag, Sn, Ta, W, Re, Os, Ir, Pt, and Au. Meanwhile, n is an integer from 1–3. In addition, L is a ligand of the formula:

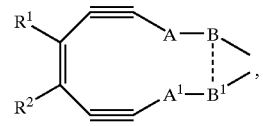

A and $A^1$ are optionally present spacers which can be the same or different and each is independently $(CR^{12}R^{13})_m$, wherein m is an integer from 0 to 6 (e.g., 0 to 3). If present, A and/or $A^1$ optionally be substituted. For example, A and $A^1$ can be optionally substituted such that $R^{12}$ and $R^{13}$ can be the same or different and each is hydrogen, halogen, amino, nitro, cyano, azido, a solubilizing group, or an organic group, such as, for example, an alkyl (e.g., $C_1$–$C_6$) or an aryl (e.g., phenyl). Examples of suitable solubilizing groups include, but are not limited to, a hydroxyl, an amino or acid addition salt thereof, an ammonium salt (e.g., quaternary ammonium salt), sulfonic acid or salt thereof, or carboxylic acid or salt thereof. In the event that $R^{12}$ and/or $R^{13}$ is an organic group (e.g., alkyl or aryl), the organic group can be unsubstituted or substituted with, for example, a halogen, nitro, cyano, azido, an organic group (e.g., alkyl or aryl) or solubilizing group, such as, for example, a hydroxyl, an amino or acid addition salt thereof, an ammonium salt (e.g., quaternary ammonium salt), sulfonic acid or salt thereof, or carboxylic acid or salt thereof.

With respect to B and $B^1$, they are the same or different and each is a nitrogen-, oxygen-, sulfur-, or phosphorus-containing substituent capable of complexing with M. The dotted line between B and $B^1$ represents an optional covalent bond. The N-, O-, S-, or P- containing groups capable of complexing with M can be cyclic or non-cyclic and can be substituted or unsubstituted.

Referring to $R^1$ and $R^2$, they can be the same or different and each independently can be hydrogen, a linear or branched alkyl (e.g., $C_1$–$C_6$), an aralkyl, an aryl, a halogen, a nitro, or a cyano, or $R^1$ and $R^2$ together with the carbons to which they are bonded can comprise an aryl, a heterocycle, a cycloalkenyl, or a macrocycle, wherein $R^1$ and $R^2$ can be unsubstituted or substituted. Strictly by way of example, cycloalkenyls can be in the form of a cyclohexene ring, cycloheptene ring, cycloheptadiene ring, cyclohexadiene ring, cyclooctene ring, cyclooctodiene ring, cyclooctotriene ring, or the like.

For clarity of description, it is to be noted that when n is greater than 1, the ligands defined by n (i.e., in the brackets) can be the same or different from each other. For example, if n=2 (i.e., there are 2 such ligands bound to M), then $R^1$, $R^2$, A, $A^1$, B and/or $B^1$ of the first ligand individually can be the same or different from $R^1$, $R^2$, A, $A^1$, B and/or $B^1$ of the second ligand.

Optionally, when n is 1 or 2, M can be complexed with at least one additional ligand other than a ligand of the formula:

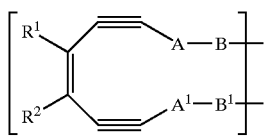

Also encompassed within the scope of the present invention are a dimer, an oligomer, or a polymer of the metalloenediyne compound.

Strictly by way of example, in some embodiments, at least one of B and $B^1$ is a nitrogen-containing group capable of complexing with M, such as, for example, a nitrogen-containing group characterized by one of the following formulas:

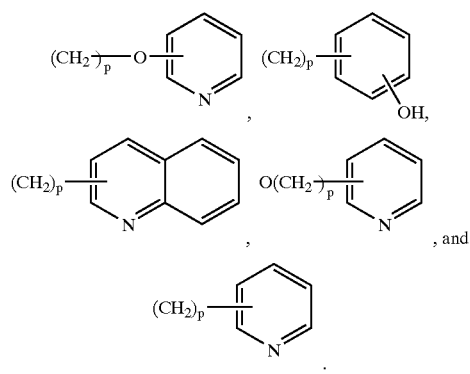

(wherein p is an integer from zero to two), such as, for example, a 3-pyridyloxy. In addition, in some embodiments, M is copper (i.e., Cu(I) or Cu(II)), m is 1, n is 2, and/or $R^1$ and $R^2$ are hydrogen.

In other embodiments, B or $B^1$ is a phosphorus-containing group capable of complexing with M. For example, the phosphorus-containing group can be a diarylphosphine such as a diphenylphosphine. Some exemplary compounds are of the formulas:

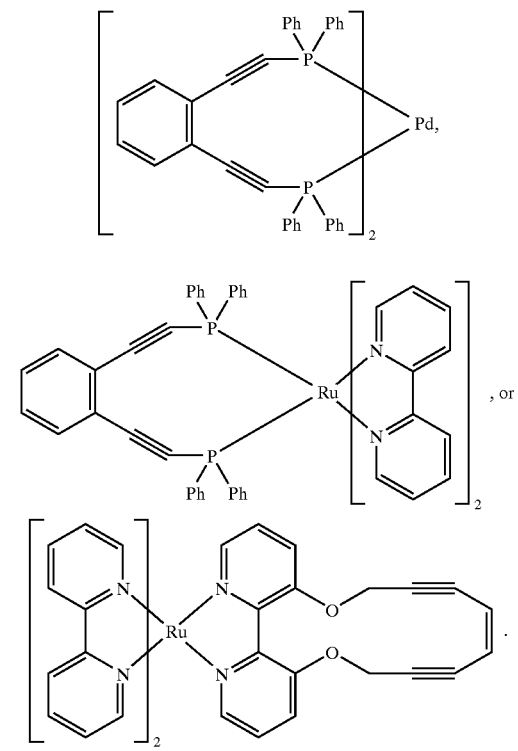

Additional exemplary enediyne ligands, in accordance with the present invention, include, but are not limited to, ligands characterized by the following formulas:

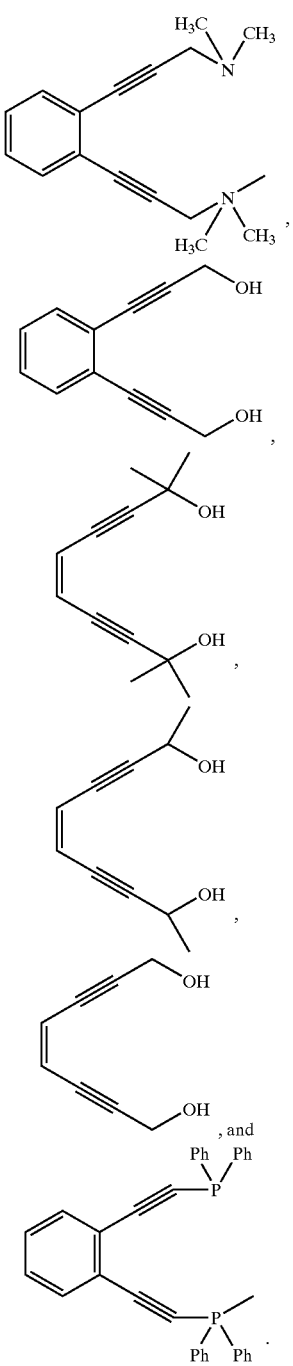

than an enediyne. The additional ligand can be, for example, a substituent of the formula:

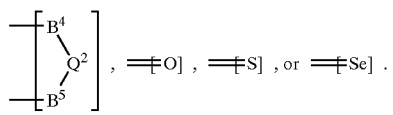

wherein $B^4$ and $B^5$ are the same or different and each is nitrogen, oxygen, sulfur, or phosphorus. $Q^2$ is an aryl, a heterocycle, a macrocycle, or a $C_2$–$C_6$ (e.g., $C_2$–$C_3$) alkyl spacer, wherein the aryl, heterocycle, or macrocycle is monocyclic or polycyclic and $Q^2$ is unsubstituted or substituted. In embodiments having an alkyl spacer, at least one hydrogen of the alkyl spacer is optionally substituted, for example, with a $C_1$–$C_6$ alkyl. In one form, $Q^2$ is an aryl.

In some embodiments where $Q^2$ is a heterocycle, the heterocycle can be bicyclic or polycyclic. Strictly by way of example, a polycyclic heterocycle suitable for $Q^2$ is characterized by the formula:

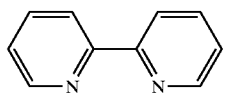

In other embodiments, the additional ligand can be a substituent characterized by the formula:

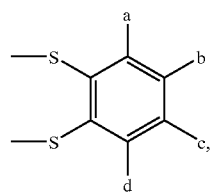

wherein a–d are the same or different and each is a hydrogen or an alkyl (e.g., $C_1$–$C_6$) . For example, in some such embodiments, the inventive compound can include at least one additional ligand of the formula:

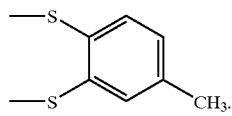

It is to be noted that, if desired, more than one additional ligand can be incorporated into a compound according to the invention.

The optional at least one additional ligand, if present, can also include a ligand of the formula:

By way of example, when $R^1$ and $R^2$ (which can be the same or different) are independently selected from the group consisting of hydrogen, an alkyl (e.g., $C_1$–$C_6$), an aryl, and an aralkyl, or, alternatively, when $R^1$ and $R^2$ (together with the carbons to which they are bonded) comprise an aryl or heterocycle, at least one of $R^1$ or $R^2$ can be optionally substituted with a substituent such as, for example, a halogen, a nitro, a cyano.

Desirably, when m is zero, B and $B^1$ are not both diphenylphosphine groups, although this embodiment may be used in the methods and compositions of the present invention.

As noted above, when n is 1 or 2, M can be optionally complexed with at least one additional auxiliary ligand other

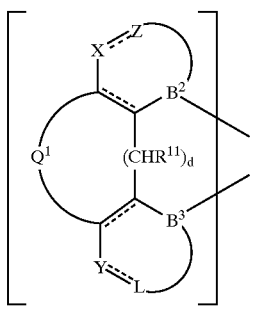

wherein $R^{11}$ is a hydrogen or a straight chain or branched alkyl;

d is zero or 1;

$B^2$ and $B^3$ are the same or different and are independently selected from nitrogen and sulfur;

Z is a contiguous linker which, together with X, $B^2$, and the carbons to which they are bonded, forms a 5- or a 6-membered heterocyclic ring;

L is a contiguous linker which, together with Y, $B^3$, and the carbons to which they are bonded, forms a 5- or a 6-membered heterocyclic ring;

the dotted lines represent double bonds optionally present in said 5- or 6-membered heterocyclic ring;

X is N, $NR^5$, or $CR^5$, wherein $R^5$ is hydrogen, halogen, or straight chain or branched alkyl;

Y is N, $NR^4$, or $CR^4$, wherein $R^4$ is hydrogen, halogen, or straight chain or branched alkyl;

$Q^1$ is an organic moiety which includes a diazo group capable of photochemically forming a radical species by the loss of $N_2$.

In addition, the at least one additional ligand can include at least one ligand of the formula:

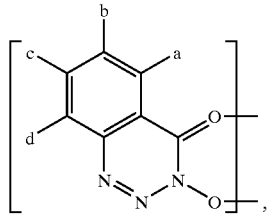

wherein a–d are the same or different and each is hydrogen, halogen, alkyl, $OR^{10}$, $SR^{10}$, nitro, and cyano, wherein $R^{10}$ is hydrogen or straight chain or branched alkyl.

In some embodiments, when n is 1 or 2, M can be optionally complexed with at least one additional ligand that comprises a macrocycle, such as, for example, a porphyrin, a porphyrazine, a chlorin, a phthalocyanine, a texaphrin, a cyclam, or a crown ether. An especially preferred macrocycle is a porphyrin or a porphyrazine. In this respect, the macrocycle can be a porphyrazine of the formula:

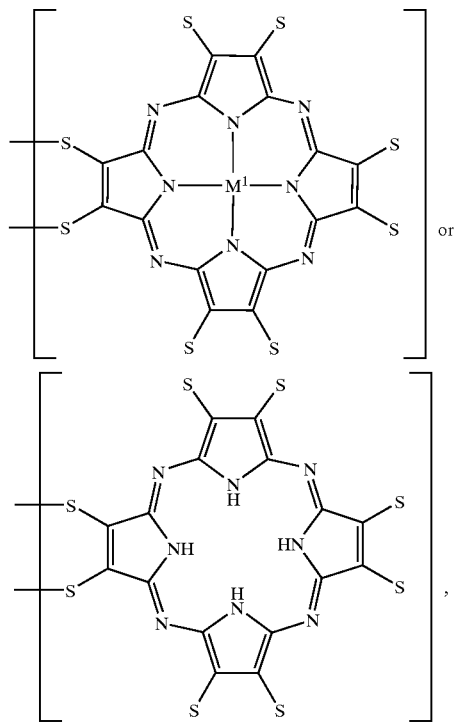

wherein the thiols located within the brackets defining the porphyrazine are uncomplexed (e.g., with an additional metal) or are optionally complexed with at least one additional metal complex of the formula:

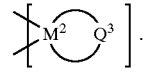

In particular, $M^1$ and $M^2$ can be the same or different and each can be a metal selected from the group consisting of Ti, V, Mn, Fe, Co, Ni, Cu, Zn, Ga, Tb, Eu, Gd, Dy, Lu, Zr, Nb, Mo, Te, Ru, Rh, Pd, Ag, Sn, Ta, W, Re, Os, Ir, Pt, and Au. Meanwhile, $Q^3$ is an enediyne of the formula:

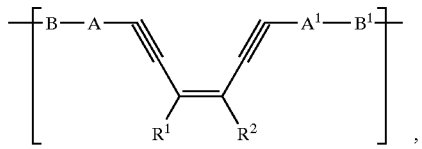

wherein:

A and $A^1$ are the same or different and each is independently $(CR^{12}R^{13})_m$, wherein m is an integer from 0 to 6 and wherein $R^{12}$ and $R^{13}$ are the same or different and each is hydrogen, halogen, nitro, cyano, azido, an optionally substituted organic group, or a solubilizing group;

n is an integer from 1–3;

B and $B^1$ are the same or different and each is a substituent comprising a nitrogen-, oxygen-, sulfur-, or phosphorus-containing group capable of complexing with M, wherein a covalent bond can be optionally present between B and $B^1$;

$R^1$ and $R^2$ are the same or different and each is independently a hydrogen, a linear or branched alkyl (e.g., $C_1-C_6$), an aralkyl, an aryl, a halogen, a nitro, or a cyano, or $R^1$ and $R^2$ together with the carbons to which they are bonded comprise an aryl, a heterocycle, or a macrocycle, wherein $R^1$ and $R^2$ is unsubstituted or substituted.

As noted above, the metalloenediyne can be in the form of a dimer, an oligomer, or a polymer. For example, with respect to dimers, the compound can be, for example, a dimer of the formula:

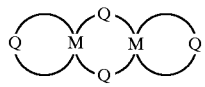

wherein Q is an enediyne of the formula:

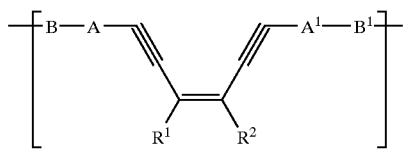

and wherein A, $A^1$, B, $B^1$, $R^1$, and $R^2$ are as defined above

By way of example, in some embodiments, the metalloenediyne is one of the following compounds:

19

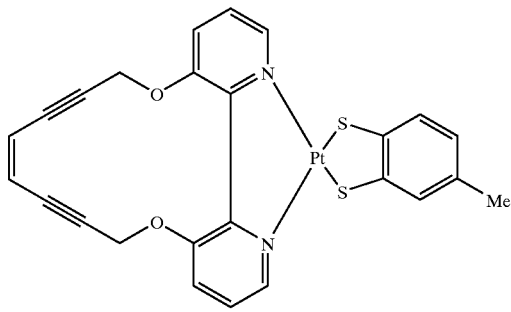

20

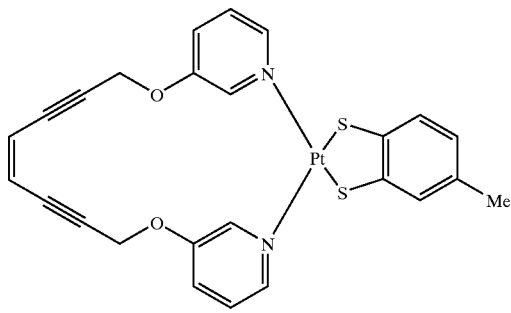

21

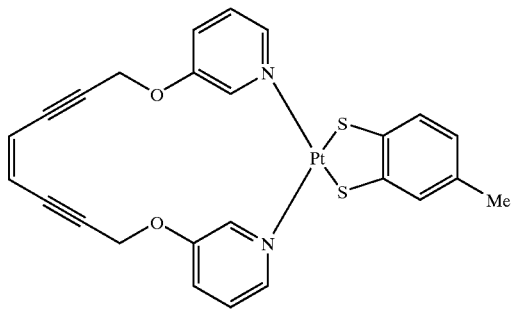

22

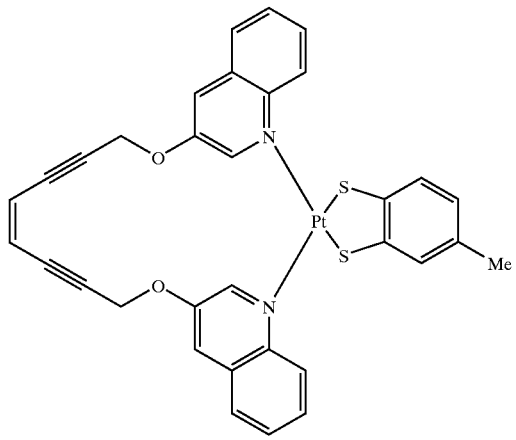

23

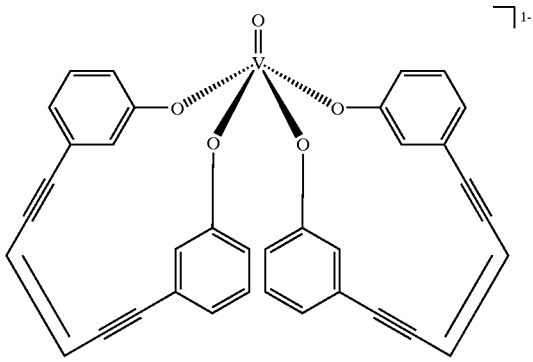

24

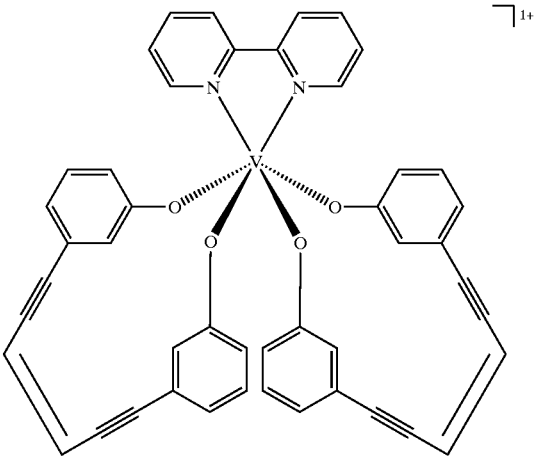

Turning now to transition metal diazo complexes, in accordance with another aspect of the present invention, a novel compound is provided having the following formula:

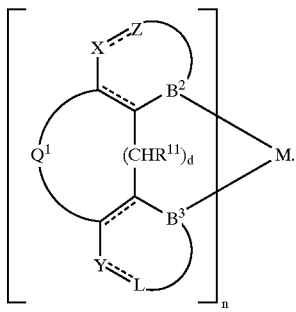

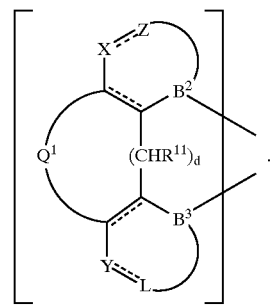

Particularly, M is a metal that is capable of complexing (as indicated), and is preferably selected from the group consisting of Ti, V, Mn, Fe, Co, Ni, Cu, Zn, Ga, Tb, Eu, Gd, Dy, Lu, Zr, Nb, Mo, Te, Ru, Rh, Pd, Ag, Sn, Ta, W, Re, Os, Ir, Pt, and Au. Meanwhile, n is an integer from 1 to 3.

The respective ring systems comprising $B^2$ and $B^3$ can be the same or different and can be separated by a bond or a one-carbon spacer (e.g., $CH_2R^{11}$). As a result, it is preferred that d is zero or 1. $B^2$ and $B^3$ can be the same or different and are independently selected from nitrogen and sulfur. $R^{11}$ can be hydrogen or a straight chain or branched alkyl (e.g., $C_1$–$C_6$).

L and Z are contiguous linkers, which, together with Y, $B^3$, and the carbons to which they are attached (in the case of L) or together with X, $B^2$, and the carbons to which they are bonded (in the case Z) form a 5 or 6-membered heterocyclic ring. In addition, X is N, $NR^5$, or $CR^5$, wherein $R^5$ is hydrogen, halogen, or $C_1$–$C_6$ straight chain or branched alkyl. Moreover, Y is N, $NR^4$, or $CR^4$, wherein $R^4$ is hydrogen, halogen, or $C_1$–$C_6$ straight chain or branched alkyl. Furthermore, the dotted lines represent double bonds optionally present in the 5- or 6-membered heterocyclic ring.

For example, and not limitation, when L is CH, Y and $B^3$ are each nitrogen, and the dotted lines represent double bonds in the ring comprising L, Y and $B^3$, then the resulting ring is a five membered heterocylic ring, namely, imidazole. Also by way of example, when L is an ethylene linker (CH=CH), Y is CH, $B^3$ is nitrogen, and the dotted lines represent double bonds in the ring comprising L, Y and $B^3$, then the resulting ring is a six-membered heterocyclic ring, namely, pyridine. Similarly, when Z is CH, X and $B^2$ are each nitrogen, and the dotted lines represent double bonds in the ring comprising X, Z, and $B^3$, then the resulting ring is imidazole. Also, when z is an ethylene linker (CH=CH), X is CH, $B^{2\ a}$ is nitrogen, and the dotted lines represent double bonds in the ring comprising X, Z, and $B^3$, then the resulting ring is pyridine.

$Q^1$ represents an organic moiety which includes a diazo group (such as, but not limited to, a terminal diazo or a diazo that is endocyclically situated, as perhaps in a triazine) which is capable of photochemically forming a radical by the loss of $N_2$.

Optionally, when n is 1 or 2, M can be complexed with at least one additional auxiliary ligand other than a diazo-containing ligand, e.g., other than a ligand of the formula:

By way of example, in some embodiments, the metal is platinum, n is 1, and/or at least one of $B^2$ and $B^3$ is nitrogen. $Q^1$ can be, for example, a substituent represented by the formula:

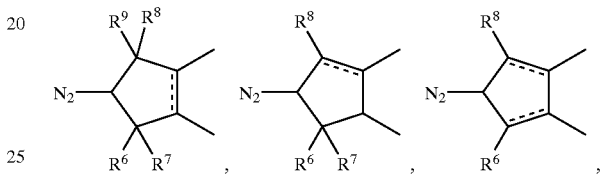

wherein $R^6$–$R^9$ are the same or different and each can be, for example, hydrogen, halogen, cyano, nitro, and straight chain or branched alkyl (e.g., $C_1$–$C_6$). The dotted lines in the ring defining $Q^1$ represent double bonds that are optionally present in the ring.

Alternatively, $Q^1$ can be a substituent represented by the formula:

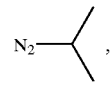

Furthermore, when n is 1 or 2, M can be optionally complexed with at least one additional ligand, such as an additional ligand of the formula:

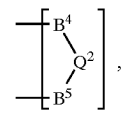

wherein $B^4$ and $B^5$ are the same or different and each is nitrogen, oxygen, sulfur, or phosphorus; and $Q^2$ is an aryl, a heterocycle, a macrocycle, or a $C_2$–$C_3$ alkyl spacer, wherein at least one hydrogen of the alkyl spacer is optionally substituted with an alkyl (e.g., $C_1$–$C_6$). For example, in one form, $Q^2$ is an aryl.

For example, the additional ligand can be of the formula:

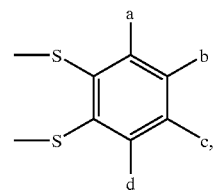

wherein a–d are the same or different and each is selected from hydrogen or straight chain or branched alkyl (e.g., $C_1$–$C_6$).

The at least one additional ligand can also include, for example, at least one ligand of the formula

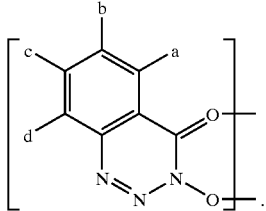

wherein a–d are the same or different and each is hydrogen, halogen, alkyl, $OR^{10}$, $SR^{10}$, nitro, and cyano, wherein $R^{10}$ is hydrogen or straight chain or branched alkyl.

In addition or as an alternative, the additional ligand can be a macrocycle, such as, for example, a porphyrin, a porphyrazine, a chlorin, a phthalocyanine, a texaphrin, a cyclam, or a crown ether. A preferred macrocycle is a porphyrin or a porphyrazine, such as, but not limited to, a porphyrazine of the formula:

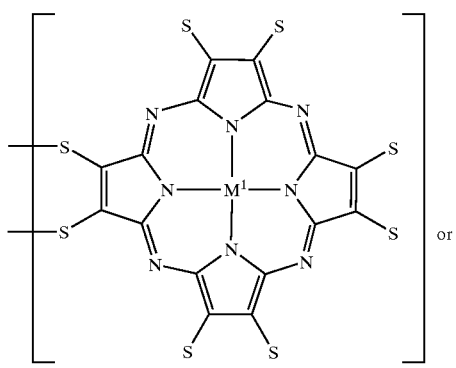

or

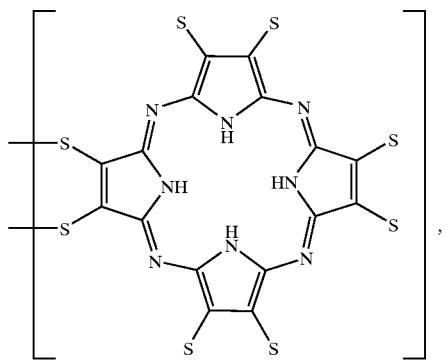

wherein the thiols located within the brackets defining the porphyrazine are uncomplexed or are optionally complexed with at least one additional metal complex of the formula:

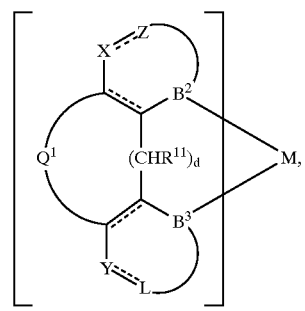

wherein M is a metal selected from the group consisting of Ti, V, Mn, Fe, Co, Ni, Cu, Zn, Ga, Tb, Eu, Gd, Dy, Lu, Zr, Nb, Mo, Te, Ru, Rh, Pd, Ag, Sn, Ta, W, Re, Os, Ir, Pt, and Au;

d is zero or 1;

$R^{11}$ is a hydrogen or a straight chain or branched alkyl (e.g., $C_1$–$C_6$);

$B^2$ and $B^3$ are the same or different and are independently selected from nitrogen and sulfur;

Z is a contiguous linker which, together with X, $B^2$, and the carbons to which they are bonded, forms a 5- or a 6-membered heterocyclic ring;

L is a contiguous linker which, together with Y, $B^3$, and the carbons to which they are bonded, forms a 5- or a 6-membered heterocyclic ring;

the dotted lines represent double bonds optionally present in the 5- or 6-membered heterocyclic ring;

X is N, $NR^5$, or $CR^5$, wherein $R^5$ is hydrogen, halogen, or straight chain or branched alkyl (e.g., $C_1$–$C_6$);

Y is N, $NR^4$, or $CR^4$, wherein $R^4$ is hydrogen, halogen, or straight chain or branched alkyl (e.g., $C_1$–$C_6$); and $Q^1$ is an organic moiety which includes a diazo group capable of photochemically forming a radical species by the loss of $N_2$.

In accordance with another aspect of the present invention, a novel transition metal diazo compound is provided characterized by the following formula:

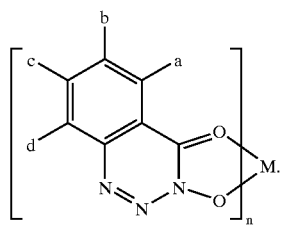

More particularly, M is a metal selected from the group consisting of Ti, V, Mn, Fe, Co, Ni, Cu, Zn, Ga, Tb, Eu, Gd, Dy, Lu, Zr, Nb, Mo, Te, Ru, Rh, Pd, Ag, Sn, Ta, W, Re, Os, Ir, Pt, and Au. Moreover, n is an integer from 1 to 3.

With respect to a–d, they can be the same or different and each can be hydrogen, halogen, $C_1$–$C_6$ alkyl, $OR^{10}$, $SR^{10}$, nitro, and cyano, wherein $R^{10}$ is hydrogen or a substituted or unsubstituted straight chain or branched alkyl (e.g., $C_1$–$C_6$).

Optionally, when n is 1 or 2, M can be complexed, if desired, with at least one additional auxiliary ligand other than a ligand of the formula:

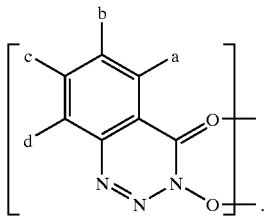

Strictly by way of example, in some embodiments, M is iron and n is 3.

When n is 1 or 2, examples of optional additional ligands to which M can be complexed include, but are not limited to, an additional ligand represented by the formula:

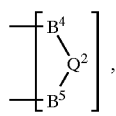

wherein $B^4$ and $B^5$ are the same or different and each is nitrogen, oxygen, sulfur, or phosphorus; and $Q^2$ is an aryl, a heterocycle, a macrocycle, or an alkyl spacer (e.g., $C_2$–$C_3$), wherein at least one hydrogen of the alkyl spacer is optionally substituted with an alkyl (e.g., $C_1$–$C_6$). In one form, $Q^2$ is an aryl.

For example, the additional ligand can be of the formula:

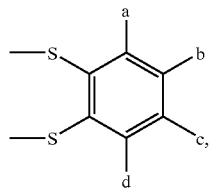

wherein a–d are the same or different and each is selected from hydrogen or a straight chain or branched alkyl (e.g., $C_1$–$C_6$).

Alternatively, the additional ligand can be a macrocycle, such as, for example, a porphyrin, a porphyrazine, a chlorin, a phthalocyanine, a texaphrin, a cyclam, or a crown ether. For example, a preferred macrocycle is a porphyrin or a porphyrazine, such as a porphyrazine of the formula:

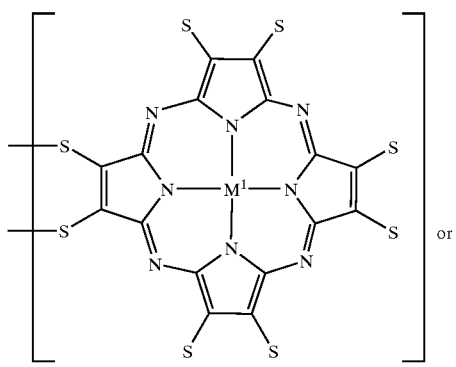

or

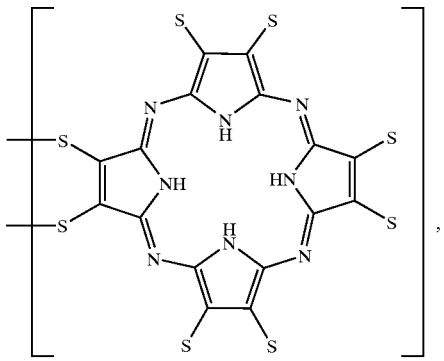

wherein the thiols located within the brackets defining the porphyrazine are uncomplexed or are optionally complexed with at least one additional metal complex of the formula:

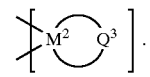

wherein $M^1$ and $M^2$ are the same or different and each is a metal selected from the group consisting of Ti, V, Mn, Fe, Co, Ni, Cu, Zn, Ga, Tb, Eu, Gd, Dy, Lu, Zr, Nb, Mo, Te, Ru, Rh, Pd, Ag, Sn, Ta, W, Re, Os, Ir, Pt, and Au; and $Q^3$ is of the formula:

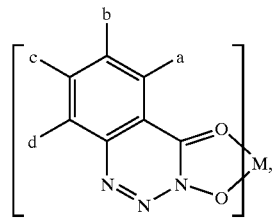

wherein M is a metal selected from the group consisting of Ti, V, Mn, Fe, Co, Ni, Cu, Zn, Ga, Tb, Eu, Gd, Dy, Lu, Zr, Nb, Mo, Te, Ru, Rh, Pd, Ag, Sn, Ta, W, Re, Os, Ir, Pt, and Au; and a–d are the same or different and each is hydrogen, halogen, alkyl (e.g., $C_1$–$C_6$), $OR^{10}$, $SR^{10}$, nitro, and cyano, wherein $R^{10}$ is hydrogen or straight chain or branched alkyl (e.g., $C_1$–$C_6$).

The present invention further provides a method of treating cancer comprising administering to a patient a therapeutically effective amount (e.g., an anticancer effective amount, such as an antitumor effective amount) of at least one compound or composition of the present invention, optionally in combination with an anticancer effective amount of at least one additional anticancer compound other than a compound of the present invention. The compound or composition can be administered, for example, orally, intramuscularly, subcutaneously, or intravenously. The composition can be present as a solution suitable, for example, for intravenous injection or infusion.

The composition also can be present in unit dosage form, such as, for example, a tablet or capsule. The therapeutically effective amount is the dose necessary to achieve an "effective level" of the active compound in the individual patient. The therapeutically effective amount can be defined, for example, as that amount required to be administered to an individual patient to achieve an anticancer effective level of a compound of the present invention to kill or inhibit the growth of the cancer; the effective level might be chosen, for example, as that level to kill or inhibit the growth of tumor cells in a screening assay. Since the "effective level" is used as the preferred endpoint for dosing, the actual dose and schedule can vary, depending upon interindividual differences in pharmacokinetics, drug distribution, and metabolism. The "effective level" can be defined, for example, as the level desired in the patient that corresponds to a concentration of a compound of the present invention which kills or inhibits the growth of human cancers in an assay which can predict for clinical anticancer activity of chemical compounds. The "effective level" for compounds of the present invention can vary when these compounds are used in combination with other anticancer compounds or combinations thereof.

Alternatively, the "effective level" can be defined, for example, as that concentration of the compound of the present invention needed to inhibit markers of the cancer in the patient's blood, or which slows or stops the growth of the patient's cancer, or which causes the patient's cancer to regress or disappear, or which renders the patient asymptomatic to the particular cancer, or which renders an improvement in the patient's subjective.sense of condition. Since a fixed "anticancer effective amount" is used as the preferred endpoint for dosing, the actual dose and schedule for drug administration for each patient can vary depending upon interindividual differences in pharmacokinetics, drug disposition, and metabolism. Moreover, the dose can vary when the compound is used in combination with other drugs.

One skilled in the art can easily determine the appropriate dose, schedule, and method of administration for the exact formulation of the composition being used, in order to achieve the desired effective level in the individual patient. One skilled in the art also can readily determine and use an appropriate indicator of the effective level of the compounds of the present invention by a direct (e.g., analytical chemistry) and/or indirect (e.g., with clinical chemistry indicators) analysis of appropriate patient samples (e.g., blood and/or tissues), or by direct or indirect observations of the shrinkage or inhibition of growth of the individual patient's tumor. There are many references in the art that teach how one works out the protocols of administering anticancer agents to patients (see, e.g., "Cancer Chemotherapy: Principles and Practice" ed., Chabner and Collins, J. B. Lippincott, 1990, especially chapter 2, by J. B. Collins).

In some embodiments, the present method of treating cancer using the compounds of the present invention can be made more effective by administering other anticancer compounds along with the compound of the present invention. These other anticancer compounds include, but are not limited to, all of the known anticancer compounds approved for marketing in the United States and those that will become approved in the future. See, for example, Table 1 and Table 2 of Boyd "The Future of Drug Development", *Current Therapy in Oncology*, Section I. Introduction to Cancer Therapy (J. E. Niederhuber, ed.), Chapter 2, by B. C. Decker, Inc., Philadelphia, 1993, pp. 11–22. More particularly, these other anticancer compounds include doxorubicin, bleomycin, vincristine, vinblastine, VP-16, VW-26, cisplatin, procarbazine, and taxol for solid tumors in general; alkylating agents, such as BCNU, CCNU, methyl-CCNU and DTIC, for brain or kidney cancers; and antimetabolites such as 5-FU and methotrexate for colon cancer.

The present invention further provides a method of treating infections by viruses and microorganisms in a host, e.g., a mammal. The specifications for the unit dosage forms of the present invention depend on the particular compound or compounds employed and the effect to be achieved, as well as the pharmacodynamics associated with each compound in the host. The dose administered should be a "therapeutically effective amount" or an amount necessary to achieve an "effective level" in the individual patient.

Since the "effective level" is used as the preferred endpoint for dosing, the actual dose and schedule may vary, depending upon interindividual differences in pharmacokinetics, drug distribution, and metabolism. The "effective level" may be defined, for example, as the blood or tissue level desired in the patient that corresponds to a concentration of one or more compounds of the invention which inhibits a microorganism or virus such as HIV in an assay known to predict for clinical antiviral activity of chemical compounds. The "effective level" for compounds which are the subject of the present invention also may vary when the compositions of the present invention are used in combination with AZT or other known antiviral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators such as p24 or RT) analysis of appropriate patient samples (e.g., blood and/or tissues).

In the treatment of some infected (e.g., virally) individuals, it may be desirable to utilize a "mega-dosing" regimen, wherein a large dose is administered, time is allowed for the compound to act, and then a suitable reagent is administered to the individual to inactivate the compound.

The pharmaceutical composition may contain other pharmaceuticals, in conjunction with the compounds of the invention to therapeutically treat acquired immunodeficiency syndrome (AIDS). Representative examples of these additional pharmaceuticals include antiviral compounds, immunomodulators, immunostimulants, and antibiotics. Exemplary antiviral compounds include 3'-azido-2',3'-dideoxythymidine (AZT), 2'3'-dideoxyinosine (ddI), 2'3'-dideoxycytidine (ddC), 2'3'-didehydro-2',3'-dideoxythymidine (D4T), 9-(1,3-dihydroxy-2-propoxymethyl)guanine (gancyclovir), fluorinated dideoxynucleotides such as 3'-fluoro-2',3-dideoxythymidine, nonnucleoside compounds such as 6,11-dihydro-11-cyclopropyl-4-methyldipyrido[2,3-b:2',3'-e]-[1,4]diazepin-6-one (nevirapine) (Shih et al., *PNAS*, 88, 9878–9882 (1991)), TIBO and analogs and derivatives such as (+)-S,4,5,6,7-tetrahydro-9-chloro-5-methyl-6-(3-methyl-2-butenyl)-imidazo[4,5,1-jk] [1,4]-benzodiazepin-2(1H)-thione (R82913) (White et al., *Antiviral Research*, 16, 257–266 (1991)), Ro 31-8959 (Craig et al., *Antiviral Research*, 16, 295–305 (1991)), BI-RJ-70 (Shih et al., *supra*), 9-(2-hydroxyethoxy-methyl)guanine (acyclovir), α-interferon, recombinant CD4 (Merigan et al., *The American Journal of Medicine*, 90 (Suppl. 4A), 8S-17S (1991)), pyridine analogs such as (3-[(benzoxazol-2-yl)ethyl]-5-ethyl-6-methylpyridin-2(1H)-one (L-696,229), 1-[(2-hydroxyethoxy)methyl]-6-phenylthiothymine (HEPT), carbocyclic 2',3'-didehydro-2',3'-dideoxyguanosine (carbovir), and [2',5'-Bis-O-(tert-butyldimethylsilyl)-β-D-ribofuranosyl]-3'-spiro-5"-(4"-amino-1",2"-oxathiole-2",2"-dioxide)thymine (TSAO-T). Exemplary immunomodulators and immunostimulants include various interleukins, CD4, cytokines, antibody preparations, blood transfusions, and cell transfusions. Exemplary antibiotics include antifungal agents, antibacterial agents, and anti-*Pneumocystis carnii* agents.

Administration of the inhibitory compound with other anti-retroviral agents and particularly with known reverse transcriptase (RT) inhibitors, such as ddC, AZT, ddI, ddA, or other inhibitors that act against other HIV proteins, such as anti-TAT agents, will generally inhibit most or all replicative stages of the viral life cycle. The dosages of ddC and AZT used in AIDS or ARC patients have been published. A virustatic range of ddC is generally between 0.05 $\mu$M to 1.0 $\mu$M. A range of about 0.005–0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently 0.01 mg/kg body weight ddC given every 8 hours is preferred. When given in combined therapy, the other antiviral compound, for example, may be given at the same time as the compound of the invention or the dosing may be staggered as desired. The two drugs also may be combined in a composition. Doses of each may be less when used in combination than when either is used alone.

Referring now to general terminology, as utilized generally herein, the term "alkyl" means a straight-chain or branched alkyl substituent containing from, for example, about 1 to about 20 carbon atoms, preferably from about 1 to about 10 carbon atoms, more preferably from about 1 to about 8 carbon atoms, still more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like. The alkyl group is preferably an alkyl group that promotes or enhances therapeutically desirable properties with respect to the compounds of the present invention, for example, anti-cancer or anti-microbial activity, metabolic stability, bioavailability, tissue distribution, improved pharmacokinetic properties, and the like, as will be appreciated by one of ordinary skill in the art.

The term "aryl" refers to an unsubstituted or substituted aromatic carbocyclic substituent, as commonly understood in the art, and includes monocyclic and polycyclic aromatics such as, for example, phenyl and naphthyl substituents, and the like.

The term "aralkyl" as utilized herein means alkyl as defined herein, wherein at least one hydrogen atom is replaced with an aryl substituent as defined herein. Aralkyls include, for example, benzyl, phenethyl, or substituents of the formula:

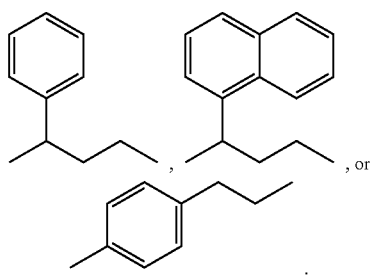

Unless otherwise indicated, at least one hydrogen on a given alkyl, aryl, heterocycle, or aralkyl substituent can be optionally substituted with an organic, inorganic, or functional group that is capable of forming a covalent bond with a carbon atom. Suitable functional groups include, for example, an alkyl, halogen, a cyano, a nitro, an amino, an amide, a hydroxy (or an ester or ether thereof), and the like.

The term "heterocycle" or "heterocyclic" encompasses both heterocycloalkyls and heteroaryls. The term "heterocycloalkyl" means a cycloalkyl substituent as defined herein (including polycyclics), wherein at least one carbon which defines the carbocyclic skeleton is substituted with a heteroatom such as, for example, O, N, or S, optionally comprising one or more double bond within the ring, provided the ring is not heteroaryl as defined herein. The heterocycloalkyl preferably has 3 to about 10 atoms (members) in the carbocyclic skeleton of each ring, preferably about 4 to about 7 atoms, more preferably 5 to 6 atoms. Examples of heterocycloalkyl substituents include epoxy, aziridyl, oxetanyl, tetrahydrofuranyl, dihydrofuranyl, piperadyl, piperidinyl, pyperazyl, piperazinyl, pyranyl, morpholinyl, and the like.

The term "heteroaryl" means a substituent defined by an aromatic heterocyclic ring, as is commonly understood in the art, including monocyclic and polyclic heteroaryls. Monocyclic heteroaryls include, for example, imidazole, thiazole, pyrazole, pyrrole, furane, pyrazoline, thiophene, oxazole, isoxazol, pyridine, pyridone, pyrimidine, pyrazine, and triazine substituents. Polycyclic heteroaryls include, for example, quinoline, isoquinoline, indole, purine, benzimidazole, benzopyrrole, and benzothiazole substituents, which heteroaryl substituents are optionally substituted with one or more substituents selected from the group consisting of a halogen, an alkyl, alkoxy, amino, cyano, nitro, and the like. It will be appreciated that the heterocycloalkyl and heteroaryl substituents can be coupled to the compounds of the present invention via a heteroatom, such as nitrogen (e.g., 1-imidazolyl).

It will also be appreciated that some polycyclic heterocyclic rings contain an aromatic ring and a non-aromatic ring. Examples of such polycyclic substituents include, for example, benzotetrahydrofuranyl, benzopyrrolidinyl, benzotetrahydrothiophenyl, and the like.

As used herein, the term "macrocycle" refers to an organic molecule (possibly complexed with one or more metals) having a large ring structure that contains at least about 15 carbons. By way of example, and not limitation, suitable macrocycles include porphyrins, porphyrazines, chlorins, phthalocyanines, texaphrins, cyclams, and crown ethers. Desirably, macrocycle-containing metalloenediyne or transition metal diazo complexes can often photochemically form radicals at wavelengths that exhibit enhanced tissue penetration of light, e.g., in the 700–850 nm range.

The following examples further illustrate the present invention, but, of course, should not be construed as in any way limiting its scope.

EXAMPLE I

This example demonstrates a procedure for making a transition metal diazo compound identified as Cu(9-diazo-4,5-diazafluorene)$_2$ (NO$_3$)$_2$.

All synthetic preparations were performed under ambient oxygen conditions. All reagents were used as purchased without further purification. 4,5-Diaza-9-fluorenone was synthesized by the oxidation of 1,10-phenathroline with KMnO$_4$ according to literature procedures, as described, for example, by L. J. Henderson, J.; Fronczek, F. R.; and Cherry, W. R., in *J. Am. Chem. Soc.* 1984, 106, 5876–5879. 4,5-diaza-9-fluorenone hydrazone was prepared by refluxing a mixture of the fluorenone and hydrazine hydrate in methanolic solution with a catalytic amount of acetic acid to prevent azine formation, as described, for example, by Mlochowski, J.; and Szulc, Z. in *Polish J. Chem.* 1983, 57, 33–39.

It is to be noted that, in terms of safety, diazo compounds are highly reactive and potentially explosive upon photo- or thermal decomposition due to the copious production of $N_2$ gas. As such, adequate protective precautions should be taken when working with them. Explosive shattering of EPR tubes upon thawing frozen photolyzed solutions of these compounds due to rapid release of the produced $N_2$ gas has been observed, so special care should be exercised under these conditions.

9-diazo-4,5-diazafluorene (diazodafene)

The hydrazone (1.00 g, 5.1 mmol) was oxidized using a basic solution (10 drops of sat'd KOH in water) of yellow HgO (1.20 g, 5.5 mmol) in benzene (200 mL), as described, for example, by Koga, N.; Ishimaru, Y.; and Iwamura, H., in *Angew. Chem. Int. Ed. Engl.* 1996, 35, 755–757.

The solution was stirred overnight at room temperature and then filtered through glass wool to remove the insoluble Hg waste. The resulting orange solution was concentrated to a solid and then recrystallized from a mixture of dichloromethane and pentane. Yield: 512 mg, 52%. Elemental analysis: Found.

(Calcd for $C_{11}H_6N_4$) C, 67.71 (67.73); H, 2.97 (3.11)); N, 24.28 (24.32). EI MS: m/z 194.1 (M+), $^1$H NMR: δ 8.72 (dd, 2H, J=1.5, 4.7 Hz) δ 7.91 (dd, 2H, J=1.5, 8.0 Hz), δ 7.39 (dd, 2H, J=4.7, 8.0 Hz). Selected IR data.

(KBr, cm$^{-1}$) 3040 (w), 2060 (vs), 1718 (w), 1593 (w), 1560 (w), 1545 (w), 1410 (s), 1394 (s), 1336 (w), 1319 (w), 1296 (m), 1262 (m), 1202 (m), 1186 (s), 1138 (w), 1099 (w), 1065 (m), 1030 (m), 801 (s), 742 (s), 702 (w), 679 (w), 625 (w), 571 (w), 489 (w), 441 (w).

Cu (diazodafene)$_2$ (NO$_3$)$_2$ 9-diazo-4,5-diazafluorene (76 mg, 0.39 mmol) was dissolved in 15 mL of methanol, keeping the flask in the dark. Cu(NO$_3$)$_2$.2.5H$_2$O (46 mg, 0.20 mmol) was dissolved in 5 mL of methanol. Both solutions were filtered through glass wool, and the Cu(NO$_3$)$_2$ solution was added to the ligand solution dropwise. The solution turned from orange to deep green and the solution was stirred for about 1 minute. The reaction mixture was allowed to stand in refrigerator or freezer overnight and then filtered to removed the microcrystalline green solid. Suitable crystals for X-ray crystallographic analysis could be grown in this manner, directly from the reaction solution. The solid was dried in vacuo for 2 h. Yield: 94 mg, 82% based on Cu. Elemental analysis: Found.

(Calcd for $C_{22}H_{12}N_{10}O_6Cu$) C, 45.90 (45.87); H 2.02 (2.10); N 24.28 (24.32). Selected IR data (KBr, cm$^{-1}$): 2081 (vs), 1589 (w), 1651 (w), 1466 (s), 1419 (m), 1396 (s), 1346 (w), 1262 (s), 1219 (w), 1188 (m), 1072 (w), 1013 (m), 802 (m), 731 (m), 684 (w), 644 (m), 571 (w), 486 (w), 432 (w).

A summary of crystallographic data is set forth in Table 1. The bond distances (Å) and angles (°) are set forth in Table 2.

TABLE 1

Summary of Crystallographic Data

| | |
|---|---|
| Empirical formula | $C_{22}H_{12}N_{10}O_6Cu$ |
| Fw | 575.95 |
| Color | Green |
| Space group | P1bar |
| a, Å | 8.897 (4) |
| b, Å | 10.178 (5) |
| c, Å | 6.833 (3) |
| α, deg | 104.47 (2) |
| β, deg | 103.31 (2) |
| γ, deg | 109.22 (2) |
| V, Å$^3$ | 531.68 |
| Z | 1 |
| T, °C. | −168 |
| l, Å | 0.711069 |
| $\rho_{calcd}$, g cm$^{-3}$ | 1.799 |
| m, cm$^{-1}$ | 10.970 |
| R (F), % | 0.0389 |
| Rw (F), % | 0.0356 |
| GOF | 1.508 |

TABLE 2

Important Bond Distances (Å) and Angles (°) in 2.

| | | | |
|---|---|---|---|
| Cu (1) | O (17) | | 2.014 (3) |
| Cu (1) | N (2) | | 1.982 (3) |
| Cu (1) ... | N (12) | | 2.651 (3) |
| N (12) | C (13) | | 1.342 (4) |
| N (15) | N (16) | | 1.136 (4) |
| O (17) | Cu (1) | O (17) | 179.96 |
| O (17) | Cu (1) | N (2) | 85.18 (10) |
| O (17) | Cu (1) | N (2) | 94.82 (10) |
| O (17) | Cu (1) | N (2) | 85.18 (10) |
| O (17) | Cu (1) | N (2) | 94.82 (10) |
| O (17) | Cu (1) ... | N (12) | 99.31 (9) |
| N (2) | Cu (1) ... | N (12) | 79.69 (10) |
| N (16) | N (15) | C (7) | 178.5 (3) |

As an alternative method, it will be appreciated that the organic synthesis for the ligands can be carried out by adding tosylhydrazide to the 4,5-diazafluoren-9-one to form the tosylhydrazone, followed by removal of the tosylalcohol leaving group upon addition of base.

EXAMPLE II

This example demonstrates an exemplary procedure for making the metalloenediyne complexes known as (1,2-bis (pyridine-3-oxy)oct-4-ene-2,6-diyne)copper(I) and (1,2-bis (pyridine 3-oxy)oct-4-ene-2,6-diyne)copper(II).

Figure 2:
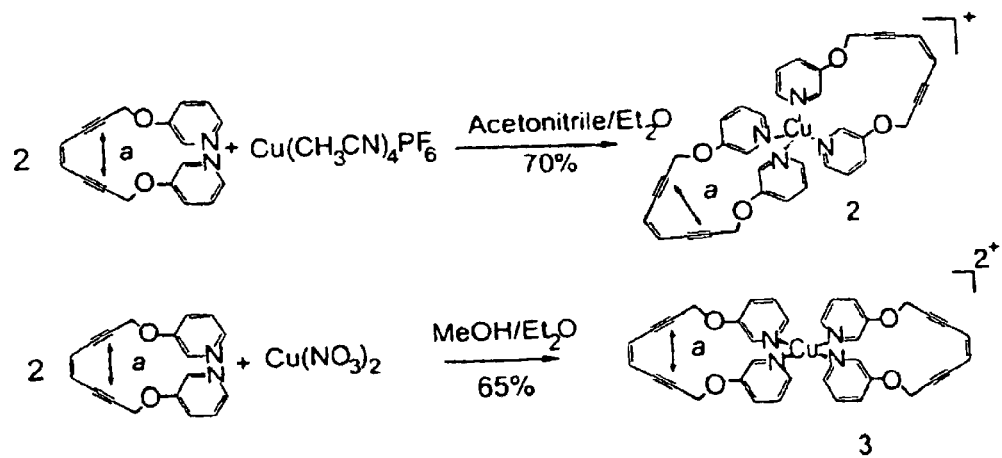
FIG. 2 schematically illustrates metal complexation reactions for the preparation of (1,2-bis(pyridine-3-oxy)oct-4-ene-2,6-diyne)copper(I), i.e., compound "2" and (1,2-bis(pyridine-3-oxy)oct-4-ene-2,6-diyne)copper(II), i.e., compound "3".

The general synthesis for the Cu(I) metal complex and Cu(II) metal complex, respectively, is illustrated in FIGS. 1 and 2.

The Cu(I) complex 2 was prepared by reacting two equivalents of compound 1 with one equivalent of Cu(CH$_3$CN)$_4$PF$_6$ in a solution of acetonitrile under nitrogen. The compound was precipitated upon addition of ether to yield the Cu(I) complex as a greenish-brown solid (yield: 55%) and characterized by conventional spectroscopic methods. [Isolated yield of 70%. Melting point (305° C. decomposes). $^1$H NMR (300 MHz DMSO-d$_6$): δ; 5.10 (s, 8H), 6.10 (s, 4H), 7.65 (m, 8H), 8.40 (br, 8H) $^{13}$C NMR (300 MHz DMSO-d$_6$): δ; 56.78, 84.78, 92.39, 120.58, 122.08, 124.54, 130.72, 138.48, 142.84, 153.83. Infrared (IR, KBr pellet): 3550, 3063, 2939, 2218 (w), 2095 (w), 1576, 1479, 1437, 1277, 1230, 999, 844. ESI ms (electrospray mass spectrometry): m/z: 643.2; 645.3 $^{63,65}$Cu[M+, calcd for $C_{36}H_{28}O_4N_4Cu$: 643.1:645.1) Elemental Analysis: calculated C(52.77); H(3.93); N(6.84) found C(52.98); H(4.08): N(6.83).] The complex is soluble in a variety of polar media and readily dissolves in water.

The Cu(II) complex was prepared by a similar approach using one equivalent of Cu(NO$_3$)$_2$.2.5H$_2$O and two equivalents of the enediyne ligand to yield 3 as a light green powder. Characterization of 3: isolated yield: 65%. Melting point (356° C. (decomposes)). $^1$H NMR (300 MHz DMSO-d$_6$)): δ 5.02–5.60 (br, 8H), 6.05–6.40 (br, 4H), 8.00–8.80 (br, 16H). Infrared (IR, KBr pellet): 3400, 3063, 2939, 2218 (w), 2090 (w), 1576. ESI ms: m/z: 643.3; 645.2 $^{63,65}$Cu [M+, calcd for C$_{36}$H$_{28}$O$_4$N$_4$Cu: 643.1: 645.1]. Elemental Analysis: calculated C (49.32); H (4.59); N (9.59) found C (49.35); H (4.17); N (8.92). The UV-Vis spectrum of 3 exhibited a broad absorption feature between 650 and 900 nm characteristic of a Cu(II) center in a tetragonal-octahedral environment, as noted by Lever, *Inorganic Electronic Spectroscopy* (Elsevier, Amsterdam, ed. 2, 1984), pp. 554–572.

The Bergman cyclization of 1–3 was studied by differential scanning calorimetry (DSC) at a heating rate of 10° C. per minute on a General V4.1C DuPont 2100 DSC differential scanning calorimeter. The free ligand 1 exhibits an exothermic peak at 258° C. corresponding to Bergman cyclization of the enediyne moiety. This value compares favorably to those reported for both the 1,2-bis(diphenylphosphinoethynyl)benzene ligand (243° C.) disclosed by B. P. Warner, S. P. Millar, R. D. Broene, S. L. Buchwald, Science, 269,814 (1995) and the bipyridine ligand (237° C.) observed by B. Konig, H. Hollnagel, B. Ahrens, P. G. Jones, Angew., Chem. Int. Ed. Engl. 34, 2538 (1995).

In contrast to the high thermal barrier for the free ligand, complexes 2 (166° C.) and 3 (135° C.) each possess a single-phase transition at dramatically reduced temperatures. The differences in the thermal reactivities of 2 and 3 can be attributed to contributions to the thermal barrier height from the geometry of the metal center. The tetrahedral structure of the Cu(I) species would be expected to require more thermal energy to reach the transition state than the square planar Cu(II) complex due to the enhanced separation of the alkyne termini ("a" in FIG. 2) based on the ~109° N—Cu—N bond angles in the structure of analogous tetrakispyridine copper(I) complexes. See, e.g., K. Nilsson and A. Oskarsson, Acta Chem. Scand. Ser. A, 36, 605 (1982). In general, these values are in the same range as those of reported for other divalent metal binding enediynes and further demonstrate the advantages of metal complexation for modulating the thermal reactivities of enediyne subunits. The reactivity of 2 and 3, however, uniquely demonstrate the additional ability to affect thermal enediyne cyclization using variations in metal oxidation state.

The thermal cyclization of 1 and 2 were also carried out in solution in the presence 1,4 cyclohexadiene (CHD) as an H-atom donor to determine the identity of the cyclized products. In a sealed NMR tube, compound 1 was heated to 140° C. in d$_6$-DMSO with a 2-fold excess of CHD. In the absence of a metal, no rearranged ligand product or decomposition occurred upon heating for 120 hours. These observations are in accordance with the thermal reactivity of 1,2 bis(diphenylphosphinoethynyl)benzene which is stable when heated at 95° C. for several days in the presence of a hydrogen donor. The thermal cyclization of 2 was also studied in solution under similar conditions by monitoring the disappearance of the olefinic protons (H$_a$) at 6.10 ppm and the appearance of the phenyl protons (H$_g$, H$_i$) at 7.32 ppm. The Cu(I) complex showed complete conversion to the Bergman cyclized product after heating at 90° C. for 8 hours.

In addition to investigating the thermal chemistry of the metal complexes as a function of oxidation state, the photochemical reactivities of enediynes 1–3 were also investigated. Compound 1 (100 mM) was anaerobically photolyzed (λ≧395 nm) for 120 hours at 0° C. in a constant temperature bath in the presence of two-fold excess hydrogen donor (CHD or isopropanol). The product of the photoreaction was extracted and showed no reactivity under these conditions as determined by $^1$H and $^{13}$C NMR. In contrast, photolysis of 2 (100 mM) generated a dark brown precipitate in 50% yield within 12 hours.

To completely identify the rearranged enediyne product, the metal was removed with ethylenediaminetetraacetic acid (EDTA) and the organic substrate extracted with dichloromethane and purified by flash chromatography. Several side products were present in very low yields and have not been identified. [Flash chromatography: (CH$_2$Cl$_2$/MeOH) light brown oil. Yield 25% in organic product, Rf: 0.47.] The Cu(I) photoproduct and the demetalled organic products (EDTA) were fully characterized ($^1$H, $^{13}$C NMR, HRMS) and determined to be Bergman cyclized products. [Characterization of Cu(I) photoproduct: $^1$H NMR (300 MHz DMSO-d$_6$): δ; 5.42 (s, 8H), 7.32 (s, 4H), 7.41 (s, 4H), 8.12 (d, 8H). $^{13}$C NMR (300 MHz.

DMSO-d$_6$): δ 70.32, 122.55, 124.90, 130.26, 134.56, 139.78, 1443.49, 155.65, ESI MS (electrospray mass spectrometry):

m/z: 647.2; 649.2 $^{63,65}$Cu[M+, cald for C$_{36}$O$_4$N$_4$Cu: 647.1:649.1.] [Characterization of organic photoproduct:

$^1$H NMR (300 MHz CD$_3$ Cl): δ; 5.21 (s, 4H) 7.21–7.25 (m, 4H) 7.40 (dd, J=3.4 Hz, 5.5 Hz, 2H) 7.51 (dd, J=3.4 Hz, 5.5.

Hz, 2H) 8.22 (d, J=16 Hz, 2H) 8.36 (d, J=1.6 Hz, 2H) 13 C.

NMR (300 MHz CD$_3$Cl): 8: 68.32, 121.41, 123.89, 128.85, 143.36, 138.06, 142.49, 154.64, HR-ms (EI-electron ionization): m/z: 292.12 [M+, calcd for C$_{18}$H$_{14}$O$_2$N$_2$: 292.141.]

Similarly, photolysis of 3 turned the bright green starting-solution to yellow-brown after only 4 hours. The photoproduct was precipitated after 12 hours with ether to yield a dark greenish brown powder in 48% yield. [Characterization of Cu(II) photoproduct; ESI MS (electrospray mass spectrometry): m/z: 647.2; 649.1 $^{63,65}$Cu[M+, calcd for C$_{36}$H$_{32}$O$_4$N$_4$Cu: 647.1: 649.1.] Subsequent extraction of the metal with EDTA confirmed the presence of the cyclized product by NMR and mass spectrometry.

Recent studies have shown that synthetic enediyne compounds may undergo Bergman cyclization upon UV-photolysis. The proposed mechanism of action is thought to involve direct excitation of an acetylenic unit at 320 nm. In light of the photochemical stability of 1 with λ≧395 nm, the facile photoinduced cyclization of these metalloenediynes at wavelengths in the visible region suggests that a metal-ligand photoredox pathway for Bergman cyclization may be operative. In fact, Chandrasekhar and colleagues have shown that rearrangements of aromatic enediynes can be realized by bimolecular thermal and photochemical redox reactions. See, D. Ramkumar et al., *J. Org. Chem*. 61, 2247 (1996).

Figure 3:
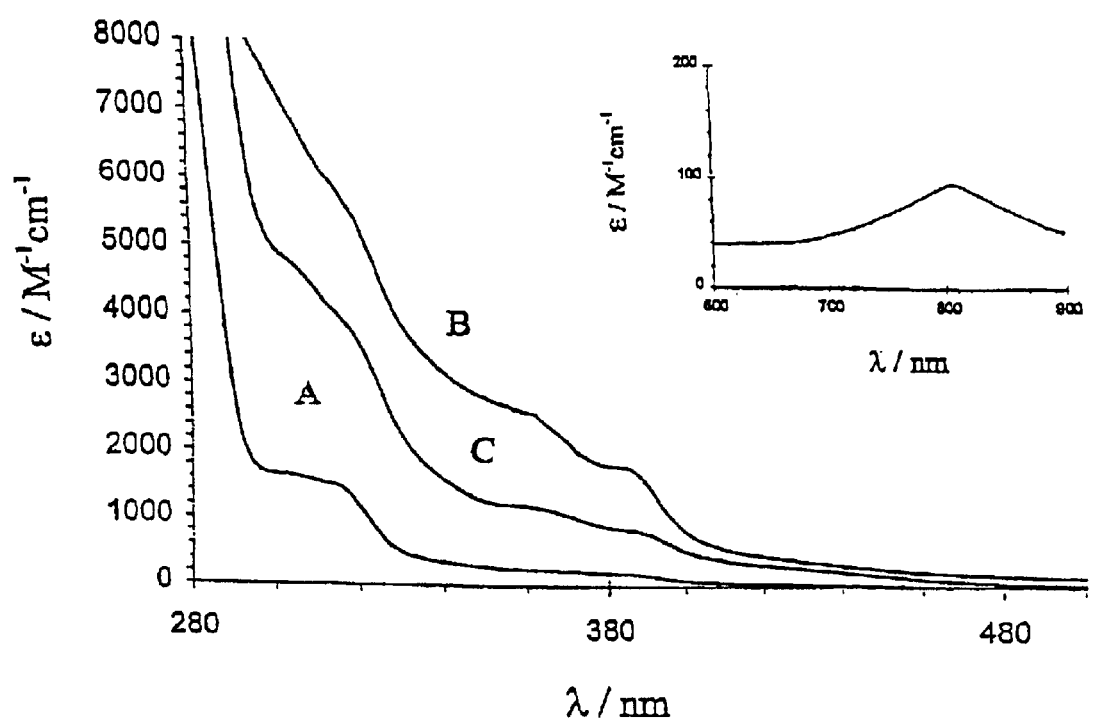
FIG. 3 illustrates a UV-Vis absorption spectrum of the enediyne ligand (compound 1), identified as "A"; (1,2-bis(pyridine-3-oxy)oct-4-ene-2,6-diyne)copper(I), identified as "B"; and (1,2-bis(pyridine 3-oxy)oct-4-ene-2,6-diyne)copper(II), identified as "C".

Supporting evidence for driving Bergman cyclization using metal-ligand photoredox reactivity of these metalloenediynes can be gained from the optical (as seen in FIG. 3) and electrochemical properties of these systems. The absorption spectrum of the Cu(I) complex shows prominent MLCT absorption features at 365 (2460 M$^{-1}$cm$^{-1}$) and 385 (1784 M$^{-1}$cm$^{-1}$) nm, respectively. These transitions correspond to Cu(dπ)→pyridine(π*) excitations and are very similar to those reported for substituted [Cu(pyridyl)$_4$]$^+$ complexes. Similarly, the Cu(II) complex displays two LMCT transitions at 363 (1180 M$^{-1}$cm$^{-1}$) and 390 nm (820 M$^{-1}$cm$^{-1}$) which are consistent with those observed for other CUN$_4$ constructs. Higher energy transitions appear in all three spectra in FIG. 3 and likely arise from ligand based ππ* transitions. The similarity in the Cu(I) and Cu(II) optical spectra can be rationalized by the low redox potential for the Cu(II)/Cu(I) couple ($E_{1/2}$=−0.12 V vs. SCE). In contrast, 1 shows irreversible electrochemical behavior upon both oxidation ($E_{1/2}$=+1.34 V vs. SCE) and reduction ($E_{1/2}$=−1.73 V vs. SCE), indicating the instability of the ligand to redox processes. This behavior is similar to that observed for simple phenyl substituted enediynes.

Complexation with either Cu(I) or Cu(II) produces no change in the reversibility of the ligand waves and only minor shifts (<0.03 V) in their potentials. Based on these values, the energy of the formal charge separated states can be approximated by the sum of the redox potentials to be $\Delta G°$=+1.46 V for the intramolecular ligand to metal photo-oxidation reaction and $\Delta G°$=+1.85 V for the metal to ligand photoreduction process. Both of these pathways are exothermic from the initially prepared charge transfer excited states which lie well above 2.0 eV. In addition, it is well known that Cu(I) and Cu(II) salts can act as catalysts for a wide variety of photoredox induced transformations of organic substrates, which further supports the instant proposed cycloaromatization scheme.

Accordingly, the preparation of novel Cu(I) and Cu(II) metalloenediyne complexes has been established in this Example. In addition, it has also been shown that their thermal reactivities are strongly influenced by the oxidation state and hence the geometry of the metal center. While highly stable in solution at ambient temperature, these complexes can be readily activated photochemically using charge transfer excitation in the visible spectral region to produce products consistent with the formation of Bergman cyclized diradical intermediates. Photochemical generation of these intermediates in the presence of bacterial plasmids results in single and double stranded DNA cleavage at physiological temperatures, as noted below. It is, therefore, expected that 2 and 3 have significant utility in treating cancers and infections caused by microorganisms. As such, this study emphasizes the utility of metalloenediyne complexes for controlling both thermal and photochemical Bergman cyclization reactions.

EXAMPLE III

This Example demonstrates the preparation, and the X-ray crystal structure and thermal reactivity of, a mononuclear Pd(O) metalloenediyne compound with two chelating 1,2-bis(diphenylphosphinoethynyl)benzene ligands (dppeb), also referred to in this Example as "the compound" or "the complex."

Figure 4A:
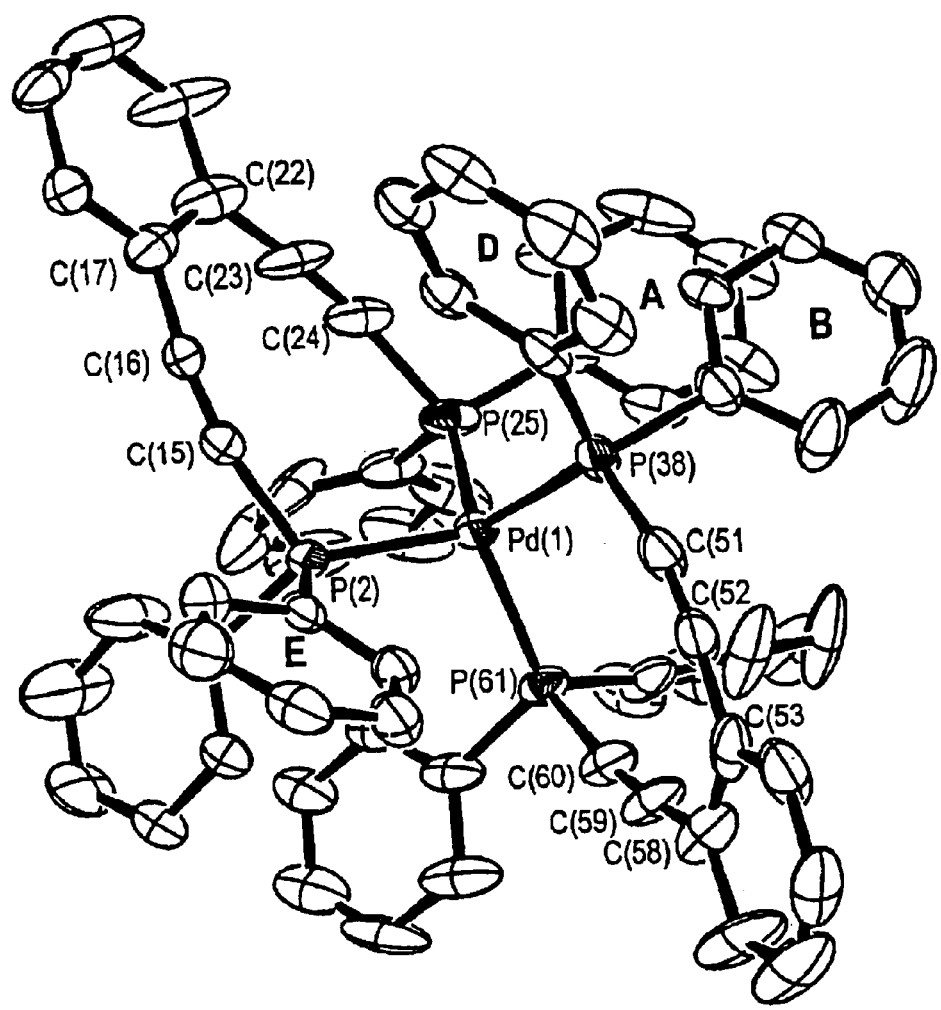
FIG. 4A represents the crystal structure of the Pd(O) bis[1,2-bis(diphenylphosphinoethynyl)benzene] enediyne compound.
Figure 4B:
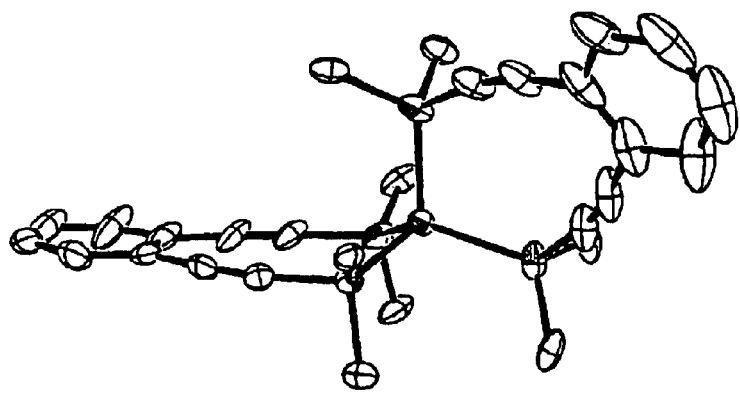
FIG. 4B represents a thermal ellipsoidal plot of the compound shown in FIG. 4A illustrating the planarity of the enediyne ligand and out-of-plane disposition (0.89 Å) of the Pd(O) center (phenyl rings removed for clarity).
Figure 14:
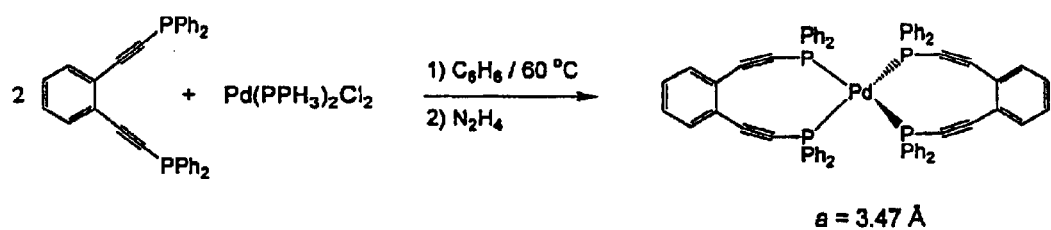
FIG. 14 illustrates the synthesis of the compound shown in FIGS. 4A and 4B (i.e., Pd(dppeb)$_2$).

This unique structure, as seen in FIGS. 4A and 4B and the synthesis of which is shown in FIG. 14, features a tetrahedral Pd center with four phosphorus atoms from two chelating ligands comprising the coordination sphere. The structure is an example of a metal-chelated enediyne compound and represents a pre-transition state structural model for in situ metal-assisted Bergman cyclization reactions. Additionally, the thermal reactivity of the compound in solution exhibits a marked increase in the temperature required for cyclization with respect to the Pd(dppeb)Cl$_2$ species. This is reflective of the increased distance of the alkyne termini promoted by the tetrahedral geometry of the d$^{10}$ Pd(O) oxidation state relative to the square planar geometry expected for the d$^8$ Pd(II) system.

The dppeb ligand was synthesized according to literature procedures, and the Pd(O) compound was prepared from a modified literature preparation. In particular, equivalents of the ligand were added to Pd(PPh$_3$)$_2$Cl$_2$ in benzene. The solution was heated and stirred at 60° C. for about 16 hours in benzene to allow complexation and was then reduced with hydrazine. Crystals of the complex suitable for X-ray diffraction were obtained within 72 hours by slow evaporation from CH$_2$Cl$_2$. The structure of the complex exhibits the typical tetrahedral coordination environment expected for a d$^{10}$ metal center with four phosphine ligands. The P—Pd—P bond angles nearly match the idealized 109.5° geometry. Of more prominent interest are the unique structural features of the metal-chelated enediyne linkage.

One of the most evident characteristics of the structure of the complex is the >$_{12}$° deviation from linearity of the P—C≡C bonds. The natural products as well as biomimetic enediynes exhibit this bending of the sp carbon that links the enediyne bridgehead to the rest of the molecule. It is apparent that the tetrahedral geometry of the metal site has imposed an additional steric demand upon the enediyne ligand, forcing a bending of the P—C≡C angle. Also noteworthy are the comparable deviations (~10°) in the C≡C—C angles of the enediyne skeleton, due presumably to an admixture of electronic and steric effects. This, too, is seen in the natural products and their analogs. Although some in-plane distortion of the enediyne ligand is observed in the structure of the complex, the alkyne carbons within each ligand are nearly eclipsed, thereby revealing no out-of-plane bending as observed in the structures of other enediyne species.

The thermal reactivity of the complex was as follows. Upon heating at 102° C. with 5 equivalents of cyclohexadiene as H-donor for 11 hours, the solution, originally orange, converted to a deep purple indicating that some reaction took place. The reaction was followed by $^{31}$p NMR analysis. The chemical shift of the complex was −5.71 ppm while that of the free ligand was −32.1 ppm. After 11 hours, there was evidence of the complex, free ligand, and 2 other resonances at −10.6 ppm and 25.4 ppm. Heating for 19 hours showed a decrease in the complex and growth in all other resonances. A shift downfield was expected for the cyclized product and this could help explain the resonance at 25.4 ppm. Likewise, from the literature, 1,2-bis (diphenylphosphino)benzene (the cyclized enediyne would be the naphthalene analog) displayed a resonance at −13 ppm which could explain the resonance at −10.6 pp. Clearly, the cyclization was not; clean. What may have happened is that a ligand dissociated from the metal after cyclizing (−10.6 ppm) and then it reassociated with the metal (25.5 ppm). From the crystal structure, the environment around the metal was strained as is evident in the Pd—P—C bending. Additionally, the bite-angle of the resulting cyclized product, 1,2-bis(diphenylphosphino)naphthalene, would be smaller than that which would be required for tetrahedral geometry. This dissociation/reassociation may be slow enough to be detected on the NMR timescale.

Comparison of the cyclization temperatures for the complex and the dichloride analog as determined by $^{31}$P NMR reveals a striking dependence of the thermal barrier on metal site geometry. Although crystallographic structural characterization of Pd(dppeb)Cl$_2$ is unavailable, the d$^8$ Pd2$^+$ geometry is likely square planar with P—Pd—P angles near 90° which would reduce the alkyne carbon termini distances and lower the thermal barrier to cyclization. It is proposed that the increase in the cyclization temperature of the complex relative to the dichloride analog may have resulted from an increased alkyne termini distance in the complex and also ligand-ligand steric interactions between the phenyl rings of the bulky phosphines. The crystal structure of the complex provides supporting evidence for this hypothesis as three unique inter-ligand phenyl ring interactions are observed. The closest contact derives from a coplanar slipped π-stacking interaction between two aromatic rings at a ~3.3 Å inter-ring separation. In a perpendicular orientation to one of these partners is an additional phenyl substituent from the second phosphine of the adjacent ligand at ~3.6 Å. A third eclipsed π interaction was observed which yielded atomic separations ranging from 4.3–6.3 Å.

Accordingly, this Example reports the first X-ray crystal structure of a chelated metalloenediyne compound. Metal chelation imposes direct steric influences upon the enediyne ligand as evidenced by the pronounced distortion from linearity of the alkyne carbons. Moreover, the local tetrahedral geometry about the Pd(O) center versus square planar Pd(II), forces the alkyne termini to a separation distance of ~3.47 Å, which yields an enediyne species that is stable at room temperature. However, the Pd(II) analog can be thermally activated at temperatures (e.g., 5° C.) at which the compound described in the present example does not undergo thermal activation. These results suggest that the steric demands introduced upon the enediyne ligand by metal chelation to Pd-centers (e.g., the distance between the reacting alkyne groups) can be strongly affected by the geometry of the metal center. Overall, this work provides conceptual insights into potential pharmaceutical opportunities for modulating enediyne reactivity using transition metals.

EXAMPLE IV

Figure 5A:
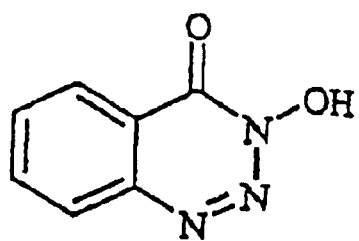
FIG. 5A shows the chemical structure of 3-Hydroxy-1,2,3-benzotriazine-4(3H)-one, also identified herein as compound "4".
Figure 5B:
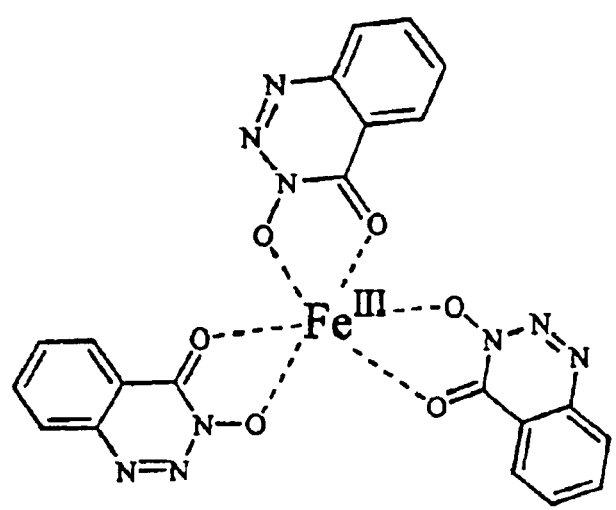
FIG. 5B shows the chemical structure of Fe(3-Hydroxy-1,2,3-benzotriazine-4(3H)-one)$_3$, also identified herein as compound "5".

This Example demonstrates the preparation of an Fe(III) triazine complex known as Fe(3-Hydroxy-1,2,3,-benzotriazine-4(3H)-one)$_3$, shown in FIG. 5B, hereinafter compound "5".

The compound 3-Hydroxy-1,2,3-benzotriazine-4(3H)-one, seen in FIG. 5A, hereinafter compound "4", is commercially available and possesses both a photoreactive N=N subunit as well as a metal coordination size, criteria, as the deprotonated 3-hydroxy-4-one functionalities are known to strongly chelate Fe(III) Furthermore, 345 nm photolysis of 4 into the n-π* transition of the triazine linkage yields a triplet EPR signal (5 K, EtOH), indicating the propensity for N$_2$ extrusion from this organic ligand. The preparation of the Fe(III) compound 5 is straightforward, as the reaction of 4 with Fe(NO$_3$)$_3$. 9(H$_2$O) in THF/Et$_3$N forms the tris(chelate) as a red powder in nearly quantitative yield. The compound afforded satisfactory analysis: calculated for FeC$_{21}$H$_{12}$N$_9$O$_6$. ½H$_2$O, Fe(10.13) C(45.75) H(2.37) N(22.87), found Fe(10.16) C(46.01) H(2.36) N(22.95). Pos. ion ESI-ms match of 543.2.

Aside from being biologically ubiquitous, Fe(III) is an ideal choice as a prototype because it is a highly active redox metal that is known to be a powerful excited state oxidant, often forming Fe(II) with ligand fragmentation. The electronic absorption spectrum of 4 in acetonitrile exhibits pronounced π-π* transitions in the 300 nm region and a shoulder at 325 nm corresponding to the forbidden diazo n-π* excitation. The absorption spectrum of 5 in the same solvent reveals three distinct bands, corresponding to a ligand-centered transition ($\lambda_{max}$=300 nm) and two moderately intense O→Fe ligand-to-metal charge transfer (LMCT) bands ($\lambda_{max}$=340, 425 nm).

Figure 6:
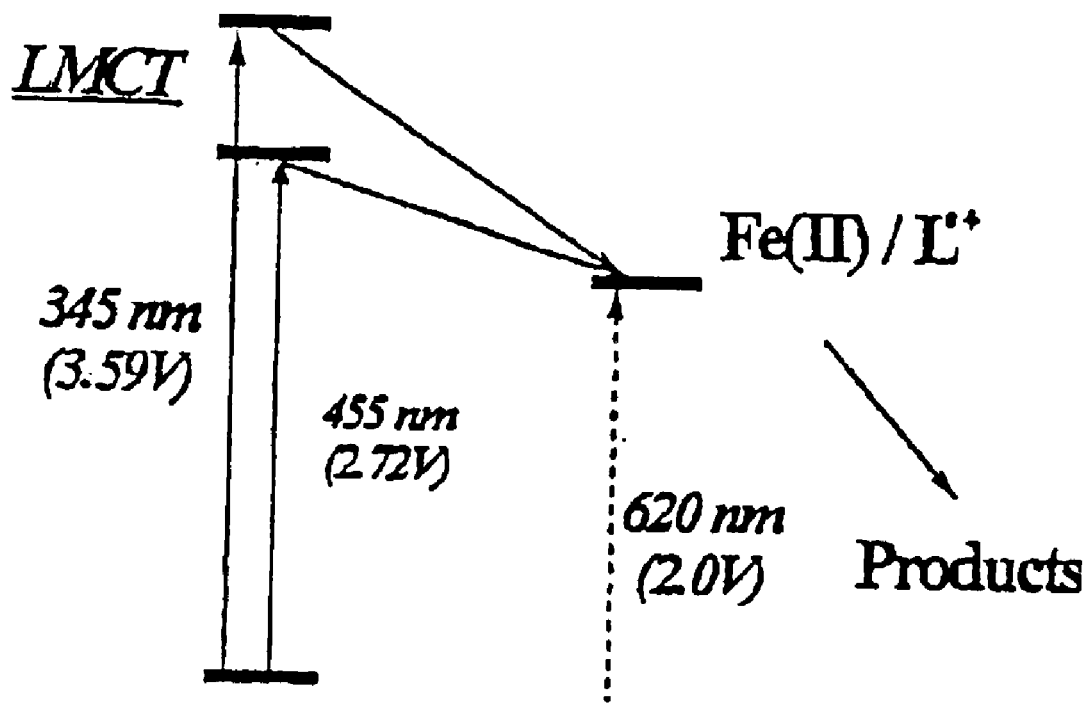
FIG. 6 illustrates an energy level diagram showing the relative energies of the optical LMCT transitions of compound 5 and the charge-separated $Fe^{2+}/L^{\cdot+}$ state.

Based on electronic structural studies of the Fe(III) tris (catecholates), the LMCT excited state of 5 is best described as a charge-separated Fe$^{2+}$/ligand radical. The energy required to photochemically produce this state (Fe$^{2+}$/L$^{*+}$, FIG. 6) can be approximated as the sum of the redox potentials for the free ligand and the metal center, where ΔE =−E$_{ox}$(4)+E$_{red}$(5). As expected, the cyclic voltammogram (CV) of 4 demonstrates an irreversible oxidation wave at a peak potential of +1.7 V vs. Ag/AgCl (E$_{ox}$(4)), consistent with rapid denitrogenation. The CV of 5 demonstrates a reversible Fe(III)/(II) redox couple with a half potential of −0.3 V vs. Ag/AgCl (E$_{red}$(5)). Thus, the minimum energy required to produce the charge-separated excited state is approximately −2.48 eV, or 500 nm.

Figure 7:
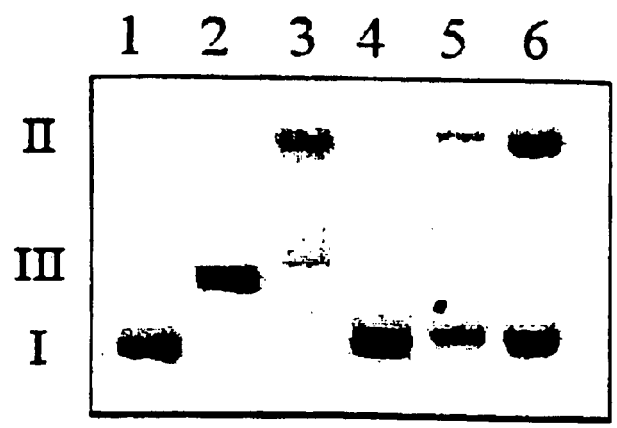
FIG. 7 depicts electronic absorption profiles of anaerobic photolyses of 0.1 nM acetonitrile solutions of compound 5 at: (a) 345 nm; and (b) 455 nm.

Although the CT excited states appeared to satisfy the energy requirement, it was unknown if sufficient excited state lifetime existed to drive photodecomposition of the ligand. To assess the reactivity of 5 at these wavelengths, acetonitrile solutions were anaerobically photolyzed with 345 nm and 455 nm filtered light and monitored with UV/Vis spectrophotometry (as seen in FIG. 7). In both cases, significant photobleaching was observed, consistent with formation of Fe(II) in solution. This observation was further supported by the reemergence of color following aerial oxidation.

Examination of FIG. 7($a$) shows that the reactivity demonstrated at early time intervals of the 345 nm photolysis is strikingly similar to that of the 455 nm photolysis, FIG. 7($b$). This similarity in the patterns of photobleaching suggests that the high and low energy photoreactions may proceed via similar reaction pathways. Both reactions exhibited first order rate behavior at early photolysis times, and not surprisingly, the 345 nm photolysis (k$_{obs}$=9.3×10$^{-2}$ min$^{-1}$) was considerably more efficient than the 455 nm photolysis (k$_{obs}$=4.0×10$^{-3}$ min$^{-1}$) under identical experimental conditions. This can be attributed to the greater extinction coefficient at 345 nm (ε=9000 M$^{-1}$cm$^{-1}$) relative to 455 nm (ε=5450 M$^{-1}$cm$^{-1}$), and the simultaneous excitation of the LMCT and n-π* transitions of the Fe(III) compound, both of which lead to denitrogenation.

To investigate this dual state hypothesis, identical photolyses were carried out on solutions of 4 in acetonitrile. The results indicated a noticeably reduced reaction rate at 345 nm and no reactivity at 455 nm. Hence, activation of the complexed ligand occurs at energies below the cutoff wavelength of the free ligand. Furthermore, reactivity of 5 has been demonstrated at wavelengths up to 515 nm, effectively ruling out the requirement for participation by higher energy excited states in the activation of the complex.

To correlate the observed reactivity with N$_2$ extrusion, a series of wavelength dependent photolyses were performed on 800 μL solutions of 5 under argon in degassed benzonitrile. From headspace GC/MS analysis, N$_2$ production was gauged by comparison of the N$_2$/O$_2$ ratios above the photolyzed samples relative to unphotolyzed controls. The average of 4 trials at each wavelength produced an increased N$_2$ content of 112% at 345 nm and 9.7% at 455 nm. Taken together, these experiments provide compelling evidence that the overall strategy to induce radical formation from CT excited states is indeed operative.

Figure 8:
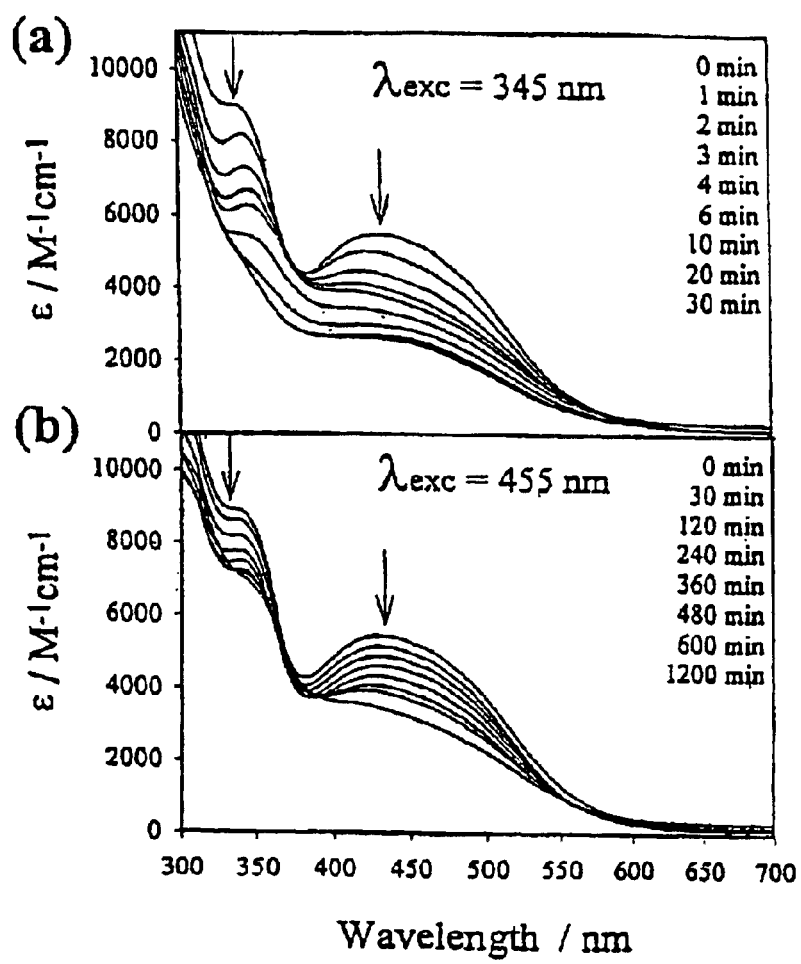
FIG. 8 illustrates the photoinduced DNA-cleavage of 30 $\mu$M/bp of pUC 118 plasmid DNA by 300 $\mu$M of compound 5 following 400 nm photolysis for 12 hours at 20° C. pursuant to 2% agarose gel electrophoresis.

In addition to possessing unique reactivity, 5 was also found to be an effective DNA photocleaver. Cleavage ability was determined by its effectiveness in converting circular supercoiled DNA (form I) to circular relaxed DNA (form II) and linear DNA (form III). FIG. 8 illustrates the agarose gel electrophoresis of photolysis products of 300 μM 5 in the presence of pUC 118 plasmid DNA (30 μM/bp). Solutions were irradiated for 12 hours in 1:9 DMSO:Tris buffer (20 mM, pH 7.55) at 400 nm. Photolyses were performed at 400

NM (rather than 455 NM) due to a soluatochronic blue shift in the optical absorption spectrum. Photolyses produced a mixture of linear and nicked forms (lane 3), while a similar thermal incubation effected no DNA cleavage (lane 4). Photolysis of the plasmid alone yielded a small amount of form II (lane 5), as did photolysis of 900 $\mu$M free ligand (lane 6). These results demonstrate that although the photoreaction of 5 did not produce exclusively linear DNA, it is the only species in FIG. 8 to produce any form III DNA and to completely consume the supercoiled form I.

Accordingly, this Example describes the facile preparation of a novel transition metal triazine compound that demonstrates unique photoreactivity. The overall strategy of metal complex activation via low energy optical excitation of LMCT transitions is indeed operative, as reactivity is observed beyond the cutoff wavelength of the free ligand. Photolyses in acetonitrile induce ligand decomposition through loss of $N_2$, resulting in the generation of ligand-based radical intermediates. Irradiation of the Fe(III) complex in the presence of plasmid DNA affords both single- and double-strand cleavage, with significantly greater efficiency than photolysis of free ligand in threefold higher concentration. This unique methodology combines the potent cleaving ability of unimolecular radical intermediates with the controlled reactivity and site selectivity of light activation. Furthermore, in contrast to many antitumor antibiotics, unimolecular activation eliminates in vivo reliance on reducing equivalents and cofactors such as $O_2$.

EXAMPLE V

This Example demonstrates the photochemical DNA-cleaving ability of the novel Cu(I) metalloenediyne complex identified herein as (1,2-bis(pyridine-3-oxy)oct-4-ene-2,6-diyne)copper(I), also identified as $[Cu(bped)2]^+$, in an anaerobic aqueous solution (10 mM Tris, pH 7.6).

Specifically, a thin layer chromatography (TLC) assay was conducted (agarose gel 2%). The $[Cu(bped)2]^+$ complex was anaerobically photolyzed with pUC118 (50 $\mu$m/base pair) at 20° C. for 12 hours and electrophoresed with supercoiled and linear plasmid controls as well as thermal incubations (aerobic and anaerobic) of the $[Cu(bped)2]^+$ complex with pUC118, as seen in FIG. 9.

Particularly, three forms of yeast bacterial plasmid DNA were prepared. Form I was supercoiled plasmid. Form II was a nicked plasmid (i.e., one of the two DNA strands was cut). Form III was a linear plasmid (i.e., both strands were cut). The three plasmid forms were then subjected to eight lanes (wells) of varying conditions. Lane 1 related to the DNA forms alone. Lane 2 involved an EcoR1 (restriction enzyme) digest of the DNA, which was used as a marker. Lane 3 subjected the DNA forms to the $[Cu(bped)2]^+$ complex in the presence of light for 12 hours at a wavelength of 400 nm. Lane 4 subjected the DNA forms to light alone, without the $[Cu(bped)2]^+$ complex. In lane 5, the DNA forms were subjected to the $[Cu(bped)2]^+$ complex and 12 hour incubation in air. Lane 6 subjected the DNA forms to the $[Cu(bped)2]^+$ complex and 12 hour incubation in $N_2$. In lane 7, the DNA forms were subjected to the copper II complex, i.e., $[Cu(bped)2]^{2+}$, and 12 hour incubation in $N_2$.

Figure 9:
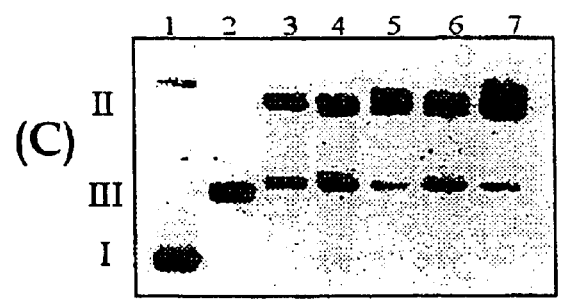
FIG. 9 illustrates the photoinduced DNA-cleavage of 50 $\mu$M pUC 118 plasmid DNA by compound 2 following 400 nm photolysis for 12 hours at 20° C. pursuant to 2% agarose gel electrophoresis.

As seen in FIG. 9, the results show that photolysis of the $[Cu(bped)2]^+$ complex (and the $[Cu(bped)2]^{2+}$ complex, gel not shown) completely consumed the supercoiled plasmid, thereby rendering a mixture of mainly linear DNA, with a measurable amount of nicked plasmid (as seen in lane 3 of FIG. 9). Meanwhile, the thermal controls show predominantly unreacted supercoiled DNA, with a small amount of nicked plasmid (as seen in lanes 4–6 of FIG. 9). It is believed that the nicked form is resulting from the reaction of Cu(I) with $O_2$ during the gel-loading period since both aerobic and anaerobic incubation lanes exhibit the nicked form in approximately comparable yields. This is supported by the lack of DNA-cleavage observed in lanes 7 and 8 from the $[Cu(bped)2]^{2+}$ complex incubated in air and under $N_2$ as controls.

Significantly, this Example demonstrates that the enediyne complexes themselves are stable in the presence of DNA for extended periods. Moreover, this Example demonstrates that the thermally stable, enediyne complexes triggered DNA-cleaving reactivity with visible photons under biologically relevant conditions.

EXAMPLE VI

Figure 10:
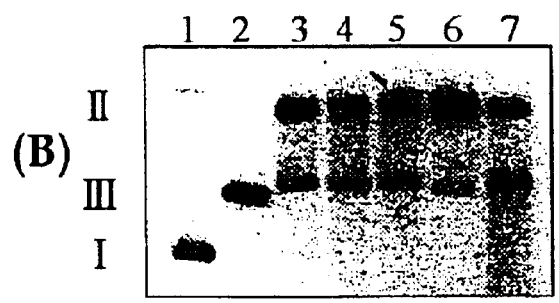
FIG. 10 illustrates DNA-cleavage of 50 $\mu$M pUC 118 plasmid DNA by bis(9-diazo-4,5-diazafluorene)copper(II) nitrate following 455 nm photolysis for 1 hour at 20° C. pursuant to 2% agarose gel electrophoresis.
Figure 10:
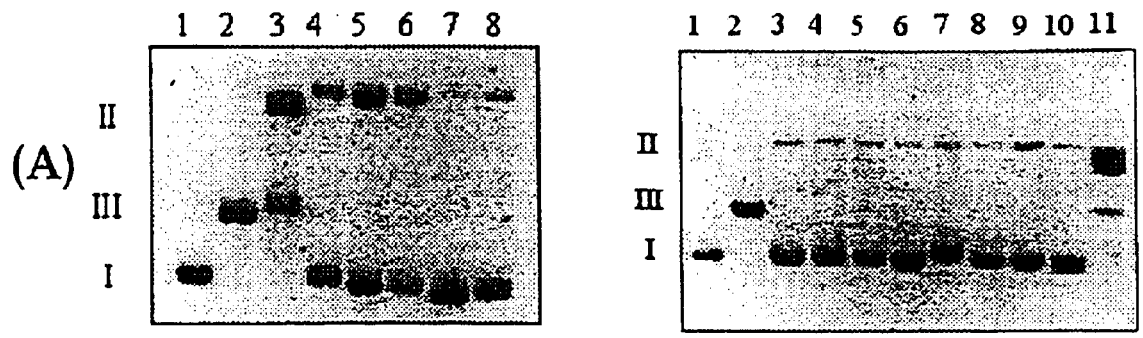

This Example demonstrates the photochemical DNA-cleaving ability of the novel Cu(II) diazo complex that possesses two 9-diazo-4,5-diazafluorene ligands, identified herein as bis(9-diazo-4,5-diazafluorene)copper(II) nitrate. FIG. 10 illustrates the DNA cleavage of 50 $\mu$M pUC118 by this compound following 455 nm photolysis for 1 hour at 20° C. (agarose gel, 2%).

Three forms of yeast bacterial plasmid DNA were prepared for use in the TLC assay. Form I was supercoiled plasmid. Form II was nicked plasmid. Form III was linear plasmid. The three plasmid forms were subjected to 11 lanes of varying conditions. Lane 1 pertained to the DNA forms alone. Lane 2 involved an EcoR1 digest of the DNA, which was used as a marker. In lane 3, the DNA was subjected for 1 hour to light at a wavelength of 455 nm. In lane 4, the DNA was subjected to 25 $\mu$m Cu(II) (diazafluorenone)$_2^{2+}$ for 1 hour incubation. In lane 5, the DNA was subjected to 25 $\mu$m Cu(II) (diazafluorenone)$_2^{2+}$ in the presence of light at a wavelength of 455 nm for 1 hour. Lane 6 subjected the DNA to 25 $\mu$m of 9-diazafluorene in the presence of light at a wavelength of 455 nm for 1 hour. In lane 7, the DNA was subjected to 25 $\mu$m 9-diazo-4,5-diazafluorene in the presence of light at a wavelength of 455 nm for 1 hour. In lane 8, the DNA was subjected to 25 $\mu$m bis(9-diazo-4,5-diazafluorene)copper(II) nitrate rapid quench. In lane 9, the DNA was subjected to 25 $\mu$m bis(9-diazo-4,5-diazafluorene) copper(II) nitrate for 1 hour incubation. In lane 10, the DNA was subjected to 25 $\mu$m bis(9-diazo-4,5-diazafluorene) copper(II) nitrate for 1 hour incubation at 37° C. In lane 11, the DNA was subjected to 25 $\mu$m bis(9-diazo-4,5-diazafluorene)copper(II) nitrate for 1 hour at a wavelength of 455 nm.

As seen in FIG. 10, after a 1-hour photolysis reaction in 10 mM Tris, pH 7.6 at 455 nm, the results of the assay demonstrate that bis(9-diazo-4,5-diazafluorene)copper(II) nitrate degrades the supercoiled plasmid pUC118 rapidly and effectively forms predominantly nicked DNA with a moderate amount of the linear form (see lane 11 of FIG. 10). Meanwhile, the thermal and photochemical control studies of DNA, Cu(II)diazafluorene, 9-diazo-4,5-diazafluorene, and bis(9-diazo-4,5-diazafluorene)copper(II) nitrate, at 20° C. (see lanes 3–11 of FIG. 10), all show very small and comparable amounts of the nicked form.

Figure 11:
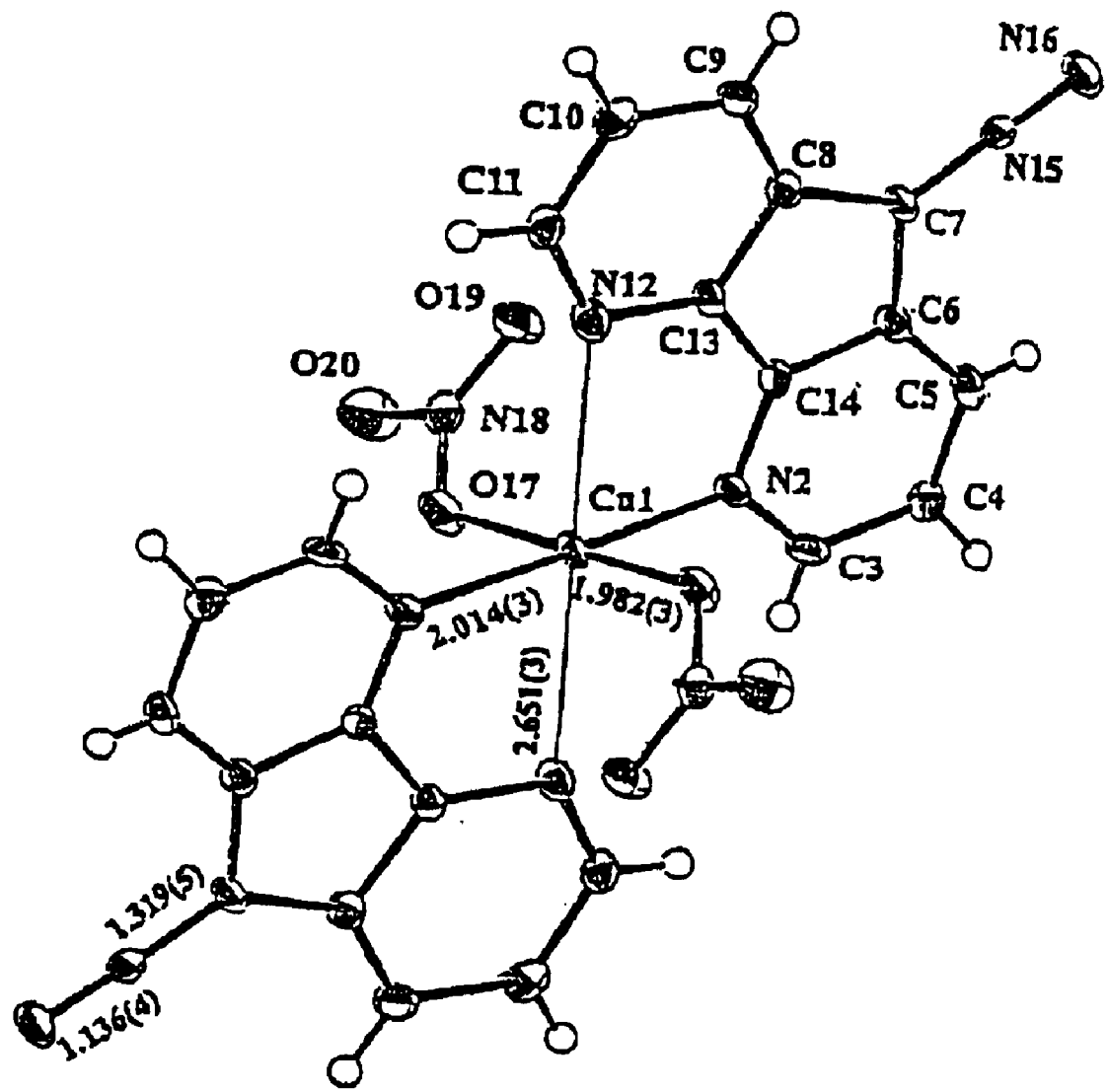
FIG. 11 represents the crystal structure of the bis(9-diazo-4,5-diazafluorene)copper(II) nitrate compound.

The detection of small amounts of nicked DNA following thermal incubations of bis(9-diazo-4,5-diazafluorene) copper(II) nitrate was not surprising since $Cu(OAc)_2$ has been known in the organic literature to thermally degrade terminal diazo groups. It is apparent from the crystal structure, shown in FIG. 11, that the preferential binding sites of the metal ion are the pyridyl nitrogens and that the DNA-cleavage reaction is driven photochemically. In addition, the free ligand, 9-diazo-4,5-diazafluorene (lanes 6 and 7), did not exhibit any preferential thermal or photochemical DNA cleavage under these reaction conditions, thereby supporting enhanced activation of the metal complex over the free ligand. It is believed that this result derives from the difference in the binding modes between 9-diazo-4,5-diazafluorene and bis(9-diazo-4,5 diazafluorene)copper (II) nitrate.

EXAMPLE VII

This example illustrates the preparation of electronic modulating metalloenediynes with extended $\pi$ structures, i.e., netalloenediynes having large chromophoric porphyrazine ligands.

Figure 12:
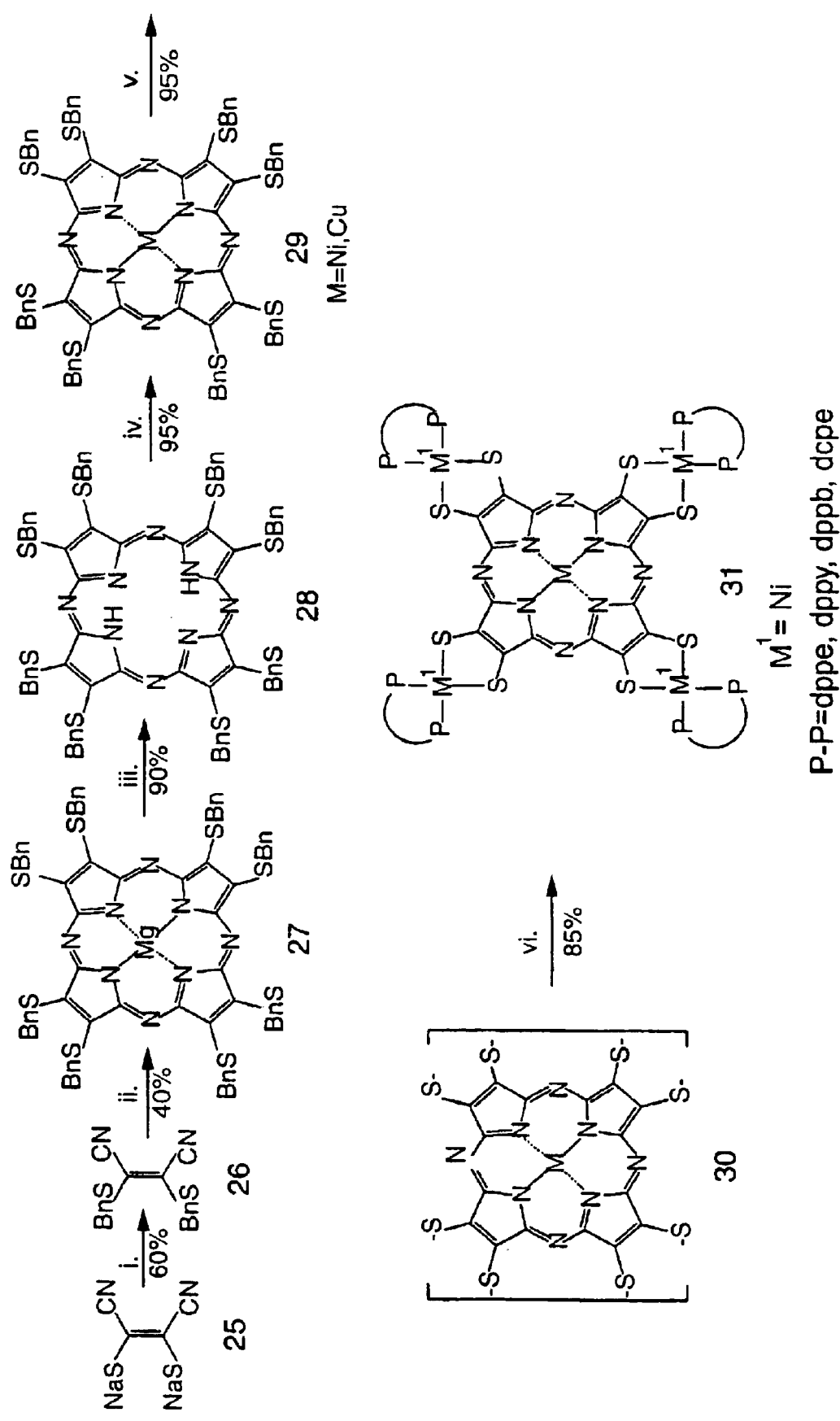
FIG. 12 illustrates an exemplary metalloenediyne-porphyrin synthesis, in accordance with the present invention.

Particularly, another approach for modulating the electronic properties of metalloenediynes is to prepare complexes with large chromophoric porphyrazine ligands, an exemplary schematic illustration thereof provided herein in FIG. 12. These metalloenediyne motifs are advantageous because the macrocycle has established $^1\pi\pi^*$ and $^3\pi\pi^*$ states (~2.2 and 1.5 eV) with high extinction coefficients (typically 70,000 $M^{-1}cm^{-1}$ at 405 nm, and 20,000 $M^{-1}cm^{-1}$ at 580–750 nm) that can be used to probe the photochemical reactivity of the adjacent enediyne ligand. By judicious choice of metal substitution at the porphyrazine center, large variations in redox potentials can be realized. In addition, for a thermally labile metal-enediyne conjugate at the periphery, the large, near-IR absorbing chromophore can be forced to non-radiatively dissipate the photochemical energy into heat, which may provide a photo-thermal temperature jump strategy for activating the enediyne ligand to undergo Bergman cyclization. The ability to use the unique porphyrazine excited states to drive enediyne cyclization either via direct redox reactions with the macrocycle, or through temperature jump thermal activation, lends insight into photocyclization of the enediynes.

The strategy for the preparation of metal-enediyne-porphyrazine conjugates has been used successfully to generate inorganic complexes that exhibit strong electronic communication between the central metal of the macrocycle and the metals bound at the periphery. In particular, the use of bidentate diphenylphosphine ligands (and the crystal structures of the resulting complexes) suggest that we should be able to use the 1,2-bis(diphenylphosphinoethynyl) benzene enediyne in place of the diphosphine ligands in order to prepare directly analogous enediyne-porphyrazine molecules. The reactivity of 1,2-bis (diphenylphosphinoethynyl)benzene enediyne is very similar to diphenylphosphinoethane (dppe) and is expected to produce the similar structures.

The synthesis proceeds principally through air-stable precursors and in relatively good yield. Referring to FIG. 12, compound 25 is prepared by reaction of sodium cyanide with carbon disulfide. Step (i) is efficient and general for a wide range of alkyl substituents. Benzyl groups are employed because of the ease of reductive Bn-S bond cleavage. Magnesium acts as a template to facilitate cyclization of the porphyrazine (tetraazaporphyrin) complex, which may be demetallated under mild conditions. Demetallation and nickel complexation are benchtop reactions common to porphyrinoid chemistry. The thiolate anion 30 is susceptible to air oxidation but can be manipulated effectively using standard Schlenk techniques. Nickel diphosphine units have been shown to chelate directly to the in situ octathiolate anion 30. The resulting complex(es) 31 is/are both air- and water-stable. Our efforts to date have now prepared 29 on the gram scale and are poised to proceed with the final capping reaction and formation of the metalloenediyne porphyrazine complexes. Although Ni(dppe)$_2$ structures are structures known to date, it is apparent that many more potential diimine dithiolate and diphosphine dithiolate analogs can be readily prepared with Pt, Cu, Ni, and Fe and other metals pursuant to the invention using our current enediyne ligands. These compounds have a number of major advantages.

For example, these compounds exhibit strong electronic communication between the central metal ion and the metal bound at the periphery. DSC and NMR characterization of the thermal reactivities of systems in this class will reflect the importance of electronic contributions from adjacent ligands to the thermal reactivity of the enediyne.

In addition, these compounds provide a mechanism to use long-lived triplet states, or higher energy singlet states to drive the enediyne cyclization reaction photochemically with systematic variations in excitation energies. The ability to tune the optical excitation energy and lifetime/energy of the excited state is critical to understanding how potential redox induced enediyne cyclization proceeds.

Furthermore, the strongly absorbing tetraazaporphyrin chromophore, coupled with a low thermal barrier to cyclization of the enediyne ligand, suggests that photoinduced temperature-jump techniques (via rapid non-radiative decay) may be useful for promoting Bergman cyclization.

The triplet state of the tetraazaporphyrin lies lower in energy than the charge separated state for direct photoredox enediyne cyclization involving Ru(II) and Pt(II) centers bound at the periphery. These metals typically have metal centered redox couples above 1.0 V and when combined with the energy required to reduce or oxidize the enediyne, approximately 2.4 eV will be required for this reaction. In other words, this redox state lies uphill from the $^3\pi\pi^*$ state (~1.8 eV) of the macrocycle. However, this is not true for the excited $^1\pi\pi^*$ states of the tetraazaporphyrin since higher energy fluorescence can be observed from these systems. Therefore, we may be able to turn-on and turn-off reactivity by choice of excitation energy. Similarly, if metals with low redox potentials such as Cu(II)/(I) are chosen, the low redox couples (~-0.3 eV), when combined with our enediyne potentials, will produce systems with downhill thermodynamics from both the $^3\pi\pi^*$ and $^1\pi\pi^*$ states.

The documented electronic communication between the central metal and those bound at the periphery strongly suggests that we will be able to use modulations in the redox properties of the central metal atom and, consequently, that of the porphyrazine ring, to drive the redox-induced enediyne cyclization photochemically. From a formal charge perspective, we will use the metallomacrocycle and not the metal bound to the enediyne as the redox source. An example of such a system is Pt(II)-metalloenediyne bound at the periphery of a Cu(II) tetraazaporphyrin. Photoinduced preparation of the $^3\pi\pi^*$ state (~1.8 eV) of macrocycle will reduce the Cu(II) to Cu(I) (~-0.3 V vs. SCE ) followed by oxidation of the enediyne bound to the copper center (+1.4 V vs. SCE). Coupling the potentials for those steps, it will cost ~1.7 V to carry out this reaction, which is nearly 734 nm. Therefore, this process is thermodynamically favored from the $^3\pi\pi^*$ state of the system and will allow us to investigate the ability to tune the redox properties of these complexes to learn whether redox chemistry is indeed at the heart of many enediyne cyclization reactions.

The large chromophore of the porphyrazine also generates opportunities for driving Bergman cyclization using optical absorption-temperature jump concepts for systems with metals at the periphery that have low thermal barriers to cyclization. Here, Pt(II)/Ni(II) conjugates may now be reactive upon $^3\pi\pi^*$ excitation, not because of redox induced cyclization, but rather via thermal heating of the porphryrazine upon optical excitation in the red spectral region. As discussed above, in these experiments, the $^3\pi\pi^*$ state will not possess sufficient energy to energy to activate the enediyne via a direct redox reaction. However, reactive Pt(II) centers with 1,2-bis(diphenylphosphinoethynyl) benzene enediyne are known to react near room temperature, thereby providing a solid starting point for triggering the enediyne by optically induced heating. These experiments may be analogous to the methods of enediyne cyclization reported in the literature for Dynemicin (quinone chromophore) and therefore an important aspect to understanding enediyne cyclization reactions.

EXAMPLE VIII

This Example describes the preparation of Ru(II) metalloenediyne complexes (six-coordinate) using nitrogen and phosphorous chelating enediyne ligands described above. From the perspective of thermal chemistry, the 6-coordinate structures will likely show diminished barriers to thermal cyclization. This in itself is a valuable study as Ru has not been examined to date as a metal cofactor to assist enediyne cyclization. However, much more valuable information can be gained about the excited state mechanism for Bergman cyclization as Ru(II) diimine compounds have an established history of MLCT photochemistry, and Ru(II) binds nitrogen and phosphorous ligands well. Moreover, by careful selection of compounds, we are able to photochemically drive redox equivalents to or away from the ligand supporting the enediyne functionality.

Figure 13:
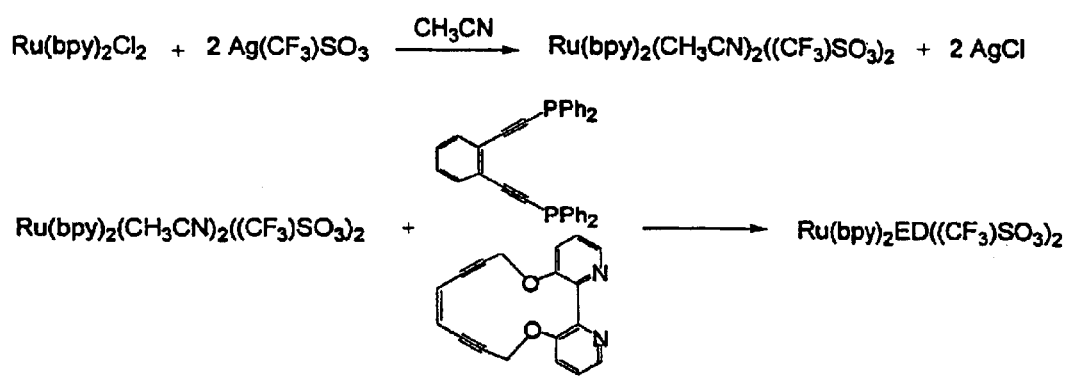
FIG. 13 illustrates an exemplary synthetic approach for preparing novel Ru(II) metalloenediynes, in accordance with the present invention.

Synthetically, the approach to preparing these complexes is to use M(phen)$_2$Cl$_2$ starting materials and react them with two equivalents of Ag(CF$_3$)SO$_3$ to precipitate out the AgCl salt, leaving the solvated metal core, as shown in FIG. 13. Using this approach, we have prepared the Ru(bpy)$_2$(ED)$^{2+}$ with 1,2-bis(diphenylphosphinoethynyl)benzene and have isolated the product in 70% yield. The product is yellow in color, and similar to the Ru(bpy)$_2$(phos)$^{2+}$ complexes. See, e.g., Sullivan et al., "Mixed Phosphine 2,2'-Bipyridine Complexes of Ruthenium," Inorg. Chem., 17, 3334–3341 (1978). The color of the complex indicates that the Ru(II) bpy MLCT transition is blue shifted due to the stabilization of the Ru d-orbitals by the σ-donating phosphine ligand. Emission from the complex is weak relative to Ru(bpy)$_3^{2+}$. Like the electronic absorption spectrum, the weak emission profile is also blue shifted relative to that of Ru(bpy)$_3^{2+}$. DSC measurements can be made and can provide immediate feedback regarding the thermal phase transition temperatures for these novel complexes. Since this complex, and those with the diimine enediyne ligands, will not be paramagnetic, $^1$H, $^{13}$C and $^{31}$P NMR will also be a very useful tool for studying the thermal reactivities of these complexes.

After preparing and characterizing the proposed Ru(II) metalloenediynes and determining their thermal cyclization temperatures by DSC and NMR, the photochemical cyclization of these complexes is probed. For example, the dependence of photoinduced cyclization on the redox potentials of the respective complexes can be probed. The Ru(II)-to-bpy MLCT excited state (τ~1 μs) and has ~2.5 eV worth of energy. We know from our electrochemical measurements that these enediyne ligands have irreversible redox potentials for oxidation between +1.2–1.4 V. With the Ru(III)/(II) couple typically ~1.3 V, MLCT photo-preparation of the Ru(III)-bpy excited state will result in oxidation of the diphenylphosphinoenediyne ligand (ED$^+$). For the photoreduction of the oxybipyridyl-enediyne (see, e.g., FIG. 13), the substituted nature of the bipyridine will cause the redox potential of the oxybipyridyl enediyne ligand to be lower than that of the unsubstituted bpy, and thus the enediyne ligand will participate directly in a photoreduction upon MLCT excitation. The oxybipyridyl enediyne ligand has an irreversible reduction at −1.4 V that will make this ligand the site of MLCT photoreduction. In a direct way, these photo-oxidation and photoreduction schemes allow us to determine whether the photochemical cyclization of the enediyne bound to the metal is a redox driven process, or simply governed by electronic modulation within the excited state. This is accomplished first using NMR to monitor the progress of the photoreaction in the presence of 1,4-cyclohexadiene, with subsequent separation and characterization of the photochemical products as we have demonstrated in our copper metalloenediyne photocyclization studies. We then employ transient absorption and luminescence lifetime measurements to evaluate the kinetics for the photoreaction process.

All of the references cited herein, including patents, patent applications, and publications, are hereby incorporated in their entireties by reference.

While this invention has been described with an emphasis upon certain preferred embodiments, it will be apparent to those of Qrdinary skill in the art that variations in the preferred compositions and methods may be used and that it is intended that the invention may be practiced otherwise than as specifically described herein. Accordingly, this invention includes all modifications encompassed within the spirit and scope of the invention as defined by the following claims.

What is claimed is:

1. A compound of the formula:

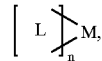

wherein M is a metal selected from the group consisting of Ti, V, Mn, Fe, Co, Ni, Cu, Zn, Ga, Th, Eu, Gd, Dy, Lu, Zr, Nb, Mo, Te, Ru, Rh, Pd, Ag, Sn, Ta, W, Re, Os, Ir, Pt, and Au;

n is an integer from 1–3;

L is a ligand of the formula:

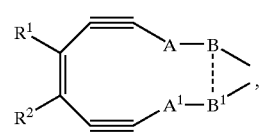

wherein A and A$^1$ are the same or different and each is independently (CR$^{12}$R$^{13}$)$_m$, wherein m is an integer from 0 to 6 and wherein R$^{12}$ and R$^{13}$ are the same or different and each is hydrogen, halogen, nitro, cyano, azido, an optionally substituted first organic group selected from the group consisting of C$_1$–C$_6$ alkyl or aryl, or a first solubilizing group selected from the group consisting of hydroxyl, an amino or acid addition salt thereof, an ammonium salt, sulfonic acid or salt thereof, or carboxylic acid or salt thereof;

B and B$^1$ are the same or different and each is a substituent comprising a nitrogen-, sulfur-, or oxygen-containing group capable of complexing with M, wherein the dotted line between B and B$^1$ represents an optional covalent bond linking B and B$^1$ together;

R$^1$ and R$^2$ are the same or different and each is independently a hydrogen, a linear or branched alkyl, an aralkyl, an aryl, a halogen, a nitro, or a cyano, or R$^1$ and R$^2$ together with the carbons to which they are bonded comprise an aryl, wherein R$^1$ and R$^2$ is unsubstituted or substituted;

wherein when n is 1 or 2, M is optionally complexed with at least one additional ligand other than a ligand of the formula:

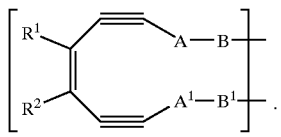

2. The compound of claim 1, wherein at least one of $R^{12}$ and $R^{13}$ is the first organic group optionally substituted with a halogen, nitro, cyano, azido, a second organic group selected from the group consisting of $C_1$–$C_6$ alkyl or aryl, or a second solubilizing group selected from the group consisting of hydroxyl, an amino or acid addition salt thereof, an ammonium salt, sulfonic acid or salt thereof, or carboxylic acid or salt thereof.

3. The compound of claim 1, wherein M is copper.

4. The compound of claim 1, wherein m is 1.

5. The compound of claim 1, wherein n is 2.

6. The compound of claim 1, wherein at least one of B and $B^1$ is a nitrogen-containing group capable of complexing with M.

7. The compound of claim 1, wherein at least one of B or $B^1$ is a nitrogen-containing group selected from the group consisting of substituents characterized by the formulas:

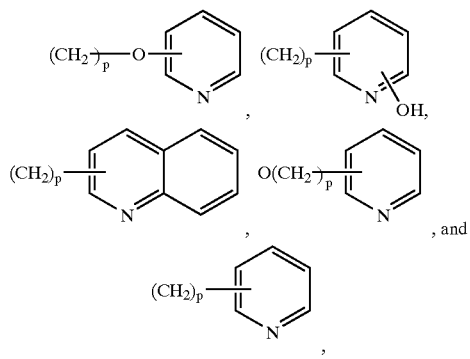

and wherein p is an integer from zero to two.

8. The compound of claim 1, wherein the compound includes at least one ligand L selected from the group consisting of:

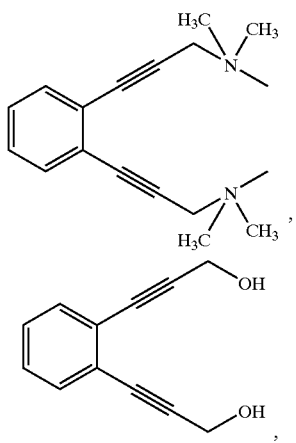

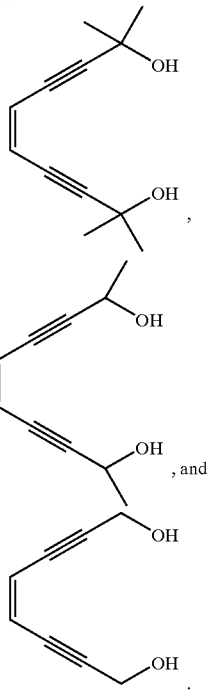

9. The compound of claim 1, wherein $R^1$ and $R^2$ are the same or different and each is independently selected from the group consisting of hydrogen, an alkyl, an aryl, and an aralkyl, or $R^1$ and $R^2$ together with the carbons to which they are bonded comprise a benzene ring.

10. The compound of claim 9, wherein at least one of $R^1$ or $R^2$ is substituted with a substituent selected from the group consisting of a halogen, a nitro, and a cyano.

11. The compound of claim 9, wherein $R^1$ and $R^2$ are hydrogen.

12. The compound of claim 1, wherein said at least one additional ligand is a substituent of the formula:

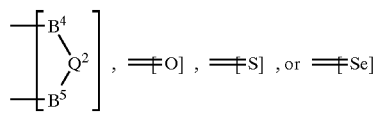

wherein $B^4$ and $B^5$ are the same or different and each is nitrogen, oxygen, sulfur, or phosphorus; and $Q^2$ is an aryl, or a $C_2$–$C_6$ alkyl spacer, wherein said aryl, is monocyclic or polycyclic and $Q^2$ is unsubstituted or substituted.

13. The compound of claim 12, wherein said at least one additional ligand is a ligand of the formula:

14. The compound of claim 12, wherein said $Q^2$ is bicyclic.

15. The compound of claim 12, wherein $Q^2$ is an aryl.

16. The compounds of claim 15, wherein said at least one additional ligand is a ligand of the formula:

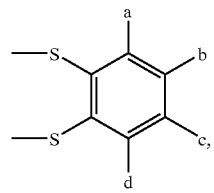

wherein a–d are the same or different and each is selected from the group consisting of hydrogen or alkyl.

17. The compound of claim 16, wherein said at least one additional ligand is a ligand of the formula

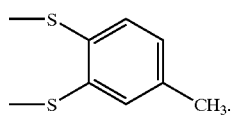

18. The compound of claim 1, wherein the compound is selected from one of the following compounds:

19

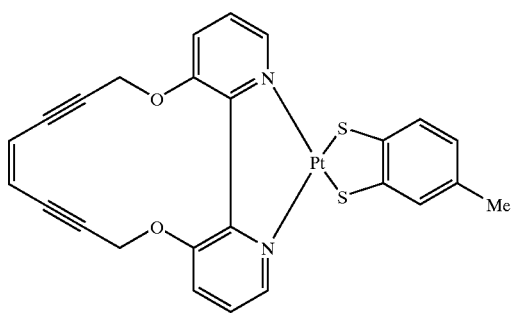

20

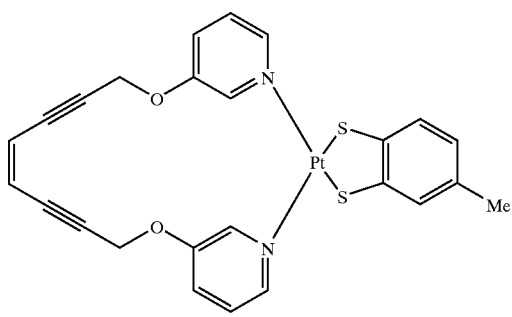

21

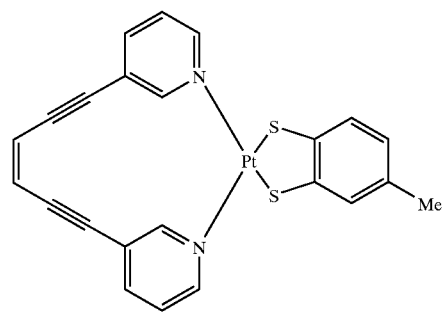

22

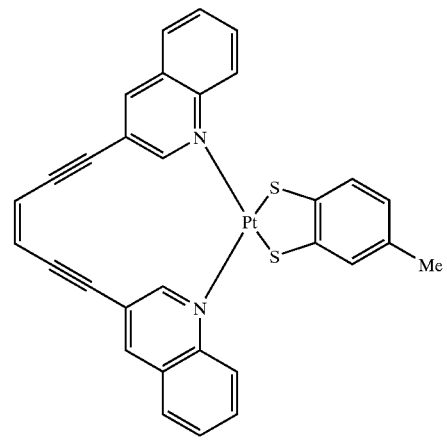

23

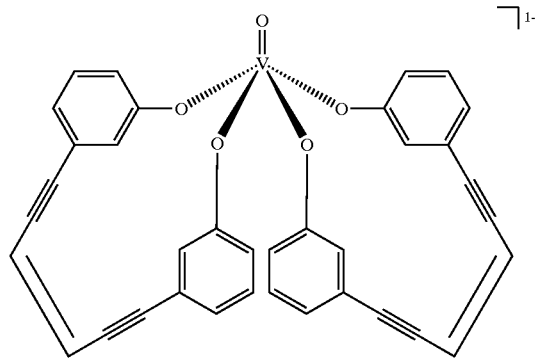

24

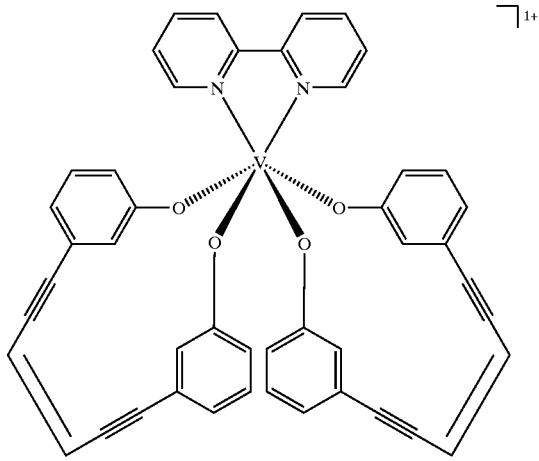

19. The compound of claim 1, wherein said compound is (1,2-bis(pyridine-3-oxy)oct-4-ene-2,6-diyne)copper(I).

20. The compound of claim 1, wherein said compound is (1,2-bis(pyridine-3-oxy)oct-4-ene-2,6-diyne)copper(II).

* * * * *